United States Patent
Ward

(10) Patent No.: US 11,441,261 B2
(45) Date of Patent: *Sep. 13, 2022

(54) SELF-STERILIZING FABRICS INCORPORATING ANTI-VIRAL COLD-ACTIVE PROTEASES

(71) Applicant: Wabeso Enhanced Enzymatics, Inc, Los Osos, CA (US)

(72) Inventor: Mandy Jane Ward, Los Osos, CA (US)

(73) Assignee: WABESO Enhanced Enzymatics, Inc., Los Osos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/467,318

(22) Filed: Sep. 6, 2021

(65) Prior Publication Data

US 2022/0074132 A1 Mar. 10, 2022

Related U.S. Application Data

(63) Continuation-in-part of application No. 17/190,299, filed on Mar. 2, 2021, which is a continuation-in-part of application No. 17/022,236, filed on Sep. 16, 2020, now Pat. No. 10,932,505, and a continuation-in-part of application No. 17/022,236, filed on Sep. 16, 2020, now Pat. No. 10,932,505.

(60) Provisional application No. 63/076,404, filed on Sep. 10, 2020.

(51) Int. Cl.
*A41D 13/11* (2006.01)
*A61P 31/12* (2006.01)
*D06M 16/00* (2006.01)
*C12N 9/54* (2006.01)

(52) U.S. Cl.
CPC ............ *D06M 16/003* (2013.01); *C12N 9/54* (2013.01); *C12Y 304/21059* (2013.01)

(58) Field of Classification Search
CPC ... A41D 13/1192; A61P 31/12; C12Y 304/00; D06M 16/003
See application file for complete search history.

(56) References Cited

U.S. PATENT DOCUMENTS

| 4,801,451 A | 1/1989 | Hellgren et al. |
| 6,485,733 B1 * | 11/2002 | Huard ............... A61L 15/34 424/443 |
| 2020/0197288 A1 | 6/2020 | Gudmundsdottir et al. |

FOREIGN PATENT DOCUMENTS

| JP | PCT/JP2009/070775 | 6/2010 |
| WO | WO2000078332 | 12/2000 |
| WO | WO2018138292 | 8/2018 |

OTHER PUBLICATIONS

Gunmunsdottir et al., Biomed. Res. Int., 2013:2013: 749078, Feb. 28, 2013 (published online).*
U.S. Appl. No. 15/115,065, filed Nov. 24, 2016, Enzymatica AB.

* cited by examiner

*Primary Examiner* — Maryam Monshipouri
(74) *Attorney, Agent, or Firm* — Adam Warwick Bell

(57) ABSTRACT

The invention provides fabrics that incorporate protease enzymes that inactivate viruses and bacteria. The fabrics of the invention may be used in the production of various items of self-sterilizing protective equipment including protective facemasks.

3 Claims, 5 Drawing Sheets

FIG. 2

| Trade Names | Source organism | Manufacturer |
|---|---|---|
| Alkaline proteases/ subtilisins | | |
| Alclase | Bacillus licheniformis | Novo Nordisk, Denmark |
| Savinase | Alkalophilic Bacillus sp. | Novo Nordisk, Denmark |
| Esperase | Alkalophilic Bacillus sp. | Novo Nordisk, Denmark |
| Liquanase | | Novo Nordisk, Denmark |
| Everlase | | Novo Nordisk, Denmark |
| Ovozyme | | Novo Nordisk, Denmark |
| Polarzyme | | Novo Nordisk, Denmark |
| Maxacal | Alkalophilic Bacillus sp. | Gist-brocades, Delft, The Netherlands |
| Maxatase | Alkalophilic Bacillus sp. | Gist-brocades, Delft, The Netherlands |
| Opticlean | Alkalophilic Bacillus sp. | Solvay Enzymes GmbH, Hannover, Germany |
| Optimase | Alkalophilic Bacillus sp. | Solvay Germany |
| Protosol | Alkalophilic Bacillus sp. | Advanced Biochemicals Ltd., Thane, India |
| Alkaline protease "Wuxi" | Alkalophilic Bacillus sp. | Wuxi Synder Bioproducers Ltd., China |
| Proleather | Alkalophilic Bacillus sp. | Amano Pharmaceuticals Ltd., Nagoya, Japan |
| Protease P | Aspergillus sp. | Amano, Japan |
| Durazym | Protein engineered variant of Savinase | Novo Nordisk, Denmark |
| Maxapem | Bleach-resistant, protein engineered variant of alkalophilic Bacillus sp. | Solvay, Germany |
| Puratect | Recombinant enzyme donor Bacillus lentus Expressed in Bacillus sp. | Genencor International Inc., Rochester, USA |
| Amylases | | |
| BAN | Bacillus amyloliquefaciens Recombinant enzyme | Novo Nordisk, Denmark |
| Termamyl | Donor- Humicola sp. Expressed in Aspergillus sp. | Novo Nordisk, Denmark |
| Staraxyme | | Novo Nordisk, Denmark |
| Duramyl | | Novo Nordisk, Denmark |
| Maxamyl | Alkalophilic Bacillus sp. | Gist-brocades, Delft, The Netherlands |
| Solvay amylase | Thermostable Bacillus licheniformis | Solvay, Germany |
| Lipases | | |
| Lipolase | Recombinant enzyme Donor- Humicola lanuginosa Expressed in Aspergillus oryzae | Novo Nordisk, Denmark |
| Lumafast | Recombinant enzyme Donor- Pseudomonas mendocina Expressed in Bacillus sp. | Genencor, USA |
| Lipoclast | NA | Advanced Biochemicals, India |
| Cellulases | | |
| Celluzyme | Humicola insolens | Novo Nordisk, Denmark |
| Endolase | | Novo Nordisk, Denmark |
| Mannanase | | |
| Mannaway | | Novo Nordisk, Denmark |
| (Novozyme report, 2006; Kumar et al., 1998). | | |

FIG. 4

| Enzyme | Function | Stains | Trade name | Manufacturer |
|---|---|---|---|---|
| Cold-active protease | Hydrolysis of peptide bonds<br>Protein stain removal | Blood stains, egg, grass, cocoa, human sweat | Kannase® Liquanase® Polarzyme® Purafectprotease® Properase® Excellase® | Novozymes<br>Novozymes<br>Novozymes<br>Palo Alto (CA, USA)<br>Genencor |
| Cold-active lipase | Hydrolysis of fats/lipids<br>Lipid stain removal | Butter, oil, sauces, cosmetics, engine oil stains | Lipoclean®<br>Lipex®, Lipolase® Ultra, Kannase, Liquanase®, Polarzyme® | Novozymes |
| Cold-active cellulase | Hydrolysis of cellulose β-glucan stain removal; removes broken cellulose fibers; color clarification; and re-deposition | Cookies, cereals, snack bars | Rocksoft™<br>Retrocell, Retrocell ZircoN Recop UTA88, 90<br>Celluzyme®<br>Celluclean® | Jupiter, FL, USA<br>EpyGen Biotech Dubai, UAE<br>Ihsan Yousefi Biochemical, Shangai, China<br>Novozymes<br>Novozymes |
| Cold-active amylase | Hydrolyzes the 1,4-α-glycosidic bond<br>Starch stain removal | Cereals, fruits, BBQ sauce, gravy, pasta | Stainzyme® Stainzyme plus® Preferenz™ S100 Purafect® | Novozymes<br>Novozymes<br>DuPont Industrial Biosciences OxAm (Genencor) |
| Cold-active mannanase | Hydrolyzes the β-1,4 bonds in mannose polymers<br>Degrade mannan or gum; mannan stain removal | Food stains, personal care, products | Mannaway®<br>Effectenz™ | Novozymes<br>DuPont |
| Cold-active pectate lyases | Hydrolysis of α-1,4 glycosidic bonds of polygalacturonic acid<br>Hydrolysis of pectin | Fruits, fruit juices, marmalades, tomato sauces | Xpect® | Novozymes |

FIG.5

SELF-STERILIZING FABRICS INCORPORATING ANTI-VIRAL COLD-ACTIVE PROTEASES

PRIORITY

This is a continuation-in-part application that claims priority to and the benefit of U.S. non-provisional application Ser. No. 17/190,299 filed 2 Mar. 2021, which claims the benefit of Ser. No. 17/022,236 filed 16 Sep. 2020, which claims benefit of U.S. provisional application 63/076,404 filed 10 Sep. 2020.

FIELD OF THE INVENTION

The embodiments of the present invention relate to fabrics into which enzymes, including psychrophilic and/or cold active enzymes, have been incorporated such that upon contact they inactivate aerosolized pathogenic microbes including enveloped viruses such as Coronavirus and Influenza virus and Gram negative bacteria. The fabrics of the invention may be used in the production of personal protective equipment (PPE) including disposable face masks, surgical gowns and head coverings, shoe coverings, clothes and bedding.

BACKGROUND

Many human illnesses are transmitted from one individual to another by aerosols or by fomites. Viruses, bacteria and prions are the causative agents of many serious diseases which cause public health emergencies and consequent economic devastation.

The 1918 Spanish flu pandemic was caused by an H1N1 influenza virus and caused about 65,000 deaths globally. Severe acute respiratory syndrome (SARS) was caused by the SARS coronavirus (SARS-CoV), and had a 9.6% fatality rate. COVID-19 first emerged in 2019 and is caused by a novel coronavirus, a positive-sense single-stranded enveloped RNA virus, the same as the SARS and MERS virus. The person-to-person transmission of viruses by aerosols and fomites is of great concern due to widespread mortality and morbidity.

Gram-negative bacilli are also a major cause of nosocomial infection in ICUs and hospitals. In 2003, gram-negative bacilli were associated with 23.8% of bloodstream infection, 65.2% of pneumonia episodes, 33.8% of surgical site infection, and 71.1% of urinary tract infection. Hospital workers need PPE that is effective in preventing the spread of nosocomial infections from patient to patient, as well as being convenient, safe, affordable, disposable, and biodegradable. See Todorova, V. et al. Gram-negative nosocomial infections in a general ICU: emerging new clues. Crit. Care 15, P224 (2011), hereby incorporated by reference.

Typical face-masks and other PPE act as fomites. Fomites are objects that when contaminated with a pathogen, can transfer it to a new host. Fabrics used in PPE have large microscopic surface areas, and act as fomites, especially in a hospital situation. When contaminated with viruses they act as a reservoir, transferring virus to hands of the user. Masks are ideal fomites. In health-care environment, self-sterilizing materials will significantly reduce nosocomial infection—a major cause of death.

Current masks concentrate particles on their surfaces, increasing the probability of introduction of an infectious dose to the user if they touch the mask and subsequently touch their nose, mouth or eyes. Breathing through a mask can become tiresome due to inherent air resistance through the fabric and moisture buildup. Air resistance and discomfort leads to frequent desire to remove or adjust the mask; therefore the mask is frequently touched, adjusted, removed, pocketed and refitted, leading to frequent handling of the contaminated outer surface.

Reducing the pore size of disposable facemasks, so that they would remove smaller virus-containing droplets, would impact the ability of the wearer to breathe, encouraging removal or adjustment of the mask. This solution would therefore be counterproductive.

Fabrics with antimicrobial additives are known. These include additives based on silver, copper, and zinc, and so called "Organic Antimicrobial Additives" that include phenolic biocides, quaternary ammonium compounds and fungicides (thiabendazole). Copper and silver-containing antimicrobial facemasks that are currently being produced reduce growth of bacteria and fungi in the mask material, but are not efficient at killing or inactivating a significant proportion of viruses entering or passing through the mask. Any killing effect that is theoretically possible is only provided on contact with the metal, and the vast majority of the surface area of such masks does not incorporate an effective proportion of metal ions. Making these masks anti-viral using this approach would require adding a proportion of metal to the material that would make the mask both extremely uncomfortable to wear and prohibitively expensive. Consequently, this solution is impractical.

There are also masks designed recently by Dibakar Bhattacharyya at the University of Kentucky that incorporate proteolytic enzymes that specifically bind to attach to the spike proteins of the coronavirus and kill the virus. Although this design is theoretically possible, there are several potential difficulties and disadvantages in the design. Firstly, these are enzymes that bind specifically to the spike-protein. These enzymes are not commercially available easily or cheaply or in large quantities. They must be created and manufactured by complex and expensive biological processes. Certainly they are not readily available in 2021 during the present COVID-19 outbreak. This contrasts with the enzymes (proteases) of the present invention which have been developed over many years for use in washing detergents or the food industry which are cheap, well-researched and dermatologically tested. Secondly, the University of Kentucky mask, when in use, will not necessarily create an appropriate chemical and osmotic environment for the proteases to adopt the correct confirmation that will be required for enzyme activity. Thirdly the University of Kentucky (UK) mask only uses specific protease enzymes that bind only to the coronavirus spike protein. It does not employ non-specific enzymes, and it does not comprise multi-enzyme blends as does the present invention. Fourth, the enzymes used in the UK mask are not and have not been designed to be active at low temperatures, such as at room temperatures, for example 10-20 degrees centigrade. Therefore they will not function efficiently as room temperatures.

Trypsins are serine proteases that cleave the peptide bond on the C-terminal side of arginine and lysine residues. They are active at neutral and alkaline pH and usually have a molecular weight of about 22-30 kDa. Trypsins have esterase and amidase activity which may be important for inactivation of viruses. Esterases cleave the ester bonds of arginine or lysine amidase—hydrolyses the C-terminal amide bond of peptides.

Cold-active trypsins are produced by many psychrophiles. Such trypsins may be isolated from the pyloric cecum and intestines of fish and the viscera of crustaceans that live in permanently cold environments. These enzymes may be described in the literature as psychrophilic and/or cold active or cold-adapted. Temperature profiles show significant activity at low temperatures, below 15, 10, 7, 5 or 2 Centigrade. While some trypsins from cold-adapted fish/crustacea may have temperature optima close to those of mammalian (mesophilic) trypsins, they retain greater activity at lower temperatures. Cold-active trypsins retain activity at below 10° C. Any individual species may produce several different trypsin isoenzymes. E.g. Atlantic cod produces several type I and type III trypsins. Trypsin I is the major trypsin, but may only be active to 10° C. Trypsins Y and ZT are active down to 2° C. and have temperature optima below those of mesophilic trypsins. Using trypsin isolated from a fish such as Atlantic cod as an anti-viral is ideal because a trypsin preparation contains a range of different trypsin isoenzymes. Trypsin sources are plentiful: Mixtures of trypsin isozymes can be extracted from cold-adapted fish or crustacean viscera. Recombinant trypsins may also be used.

The genus *Gadus* (e.g., Cod) includes psychrophiles thriving permanently at near-zero temperatures which synthesize cold-active enzymes to sustain their cell cycle. Most psychrophilic enzymes optimize a high activity at low temperature at the expense of substrate affinity, therefore reducing the free energy barrier of the transition state. Furthermore, a weak temperature dependence of activity ensures moderate reduction of the catalytic activity in the cold. In these naturally evolved enzymes, the optimization to low temperature activity is reached via destabilization of the structures bearing the active site or by destabilization of the whole molecule. This involves a reduction in the number and strength of all types of weak interactions or the disappearance of stability factors, resulting in improved dynamics of active site residues in the cold.

These enzymes are already used in many biotechnological and commercial applications requiring high activity at low temperatures. However they have not been incorporated into fabrics for PPE.

The fabrics of the present invention may also be used for dressings for wound debridement, or in other embodiments, specifically exclude use for wound debridement.

A number of particularly relevant disclosures and publications are set out below, and are all incorporated by reference for all purposes. U.S. Pat. Nos. 4,801,451 and 4,963,491 disclose a mixture of exo- and endopeptidases isolated from Antarctic hill (*Euphasia superba*) and the use of this mixture as a cleaning solution. U.S. Pat. No. 4,801,451 discloses the use of such enzymes to remove foreign matter and dead tissue from wounds. WO 85/04809 discloses the use of hill enzymes as a digestion-promoting agent. EP-A1-0170115 discloses the use of krill enzymes to dissolve blood clots. WO96/24371 discloses the use of a hill-derived multifunctional proteolytic enzyme and a family of crustacean and fish derived proteolytic enzymes having structural similarity to the multifunctional enzyme derived from Antarctic hill. The document also relates to cosmetic and other uses of the enzyme. WO2000078332 discloses the use of cod derived trypsins and chymotrypsins in pharmaceutical compositions or medicaments for local and topical application. The serine proteinases disclosed in WO 2000078332 are proteinases that have at least 90% amino acid sequence homology with trypsin I, trypsin II, trypsin III, trypsin IV derived from Atlantic cod and proteinases that are chymotrypsin having at least 90% amino acid sequence homology with any of chymotrypsin A and chymotrypsin B isolated from Atlantic cod. Spilliaert and Gudmundsdottir, 1999, Mar Biotechnol (NY) 1: 598-607 discloses a cDNA encoding trypsin Y isolated from an Atlantic cod cDNA library. Cod trypsin Y has approximately 45% identity to the two Atlantic cod trypsin I and X (WO 2000078332). The native trypsin Y and recombinant forms of trypsin Y have previously briefly been described by Palsdottir and Gudmundsdottir, 2007, Protein Expr Purif 51: 243-252, and Palsdottir and Gudmundsdottir, 2008, Food Chemistry 111: 408-414. WO2018138292A1 (to Enzymatica Ab) describes a marine serine protease that is a trypsin, for example trypsin I, trypsin X, trypsin Y or trypsin ZT. Three major isozymes of trypsin were originally characterized from Atlantic cod, designated Trypsin I, II and III (see Asgeirsson et ai, 1989, Eur. Priority 2017-Jan.-26•Filed 2018-Jan.-26•Published 2018-Aug.-2. WO2018138292A1 discloses polypeptides having protease activity for use in the treatment or prevention of otitis. In one embodiment, the polypeptide consists of an amino acid sequence of trypsin I from Atlantic cod (*Gadus morhua*).

Other particularly relevant patent applications include: US2020/0197288 (Novel trypsin isoforms and their use) and US2016/0339087 which discloses a polypeptide comprising an amino acid sequence of SEQ ID NO: 1 (see published application) or a fragment, variant, derivative or fusion thereof which retains the trypsin activity. Other related applications and patents include U.S. Ser. No. 15/115,065 and PCT/GB2015/050212. A publication of particular relevance is Stefannson, B., A. Gudmundsdottir and M. Clarsund. (2017) A medical device forming a protective barrier that deactivates four major common cold viruses. Virol. Res. Rev. 1(5):1-3. Other relevant disclosures include the following: 20210130852, Device and method for increasing the organic yield of a bioliquid; 20200353060, Peptides having protease activity for use in the treatment or prevention of coronavirus infection; 20200197288, Novel trypsin isoforms and their use; 20200085921, Combination therapies; 20190375664, Methods of processing municipal solid waste (msw) using microbial hydrolysis and fermentation; 20190343932, Novel treatments; 20160339087, Novel treatments; and 20170107503, which discloses recombinantly expressed mutants of trypsin I from Atlantic cod, which mutants exhibit improved stability and/or catalytic properties relative to the wildtype trypsin purified from cod. These and all other patents, applications and publications herein are incorporated by reference.

There is a long-felt need, with a particular new urgency, for fabrics that are self-sterilizing, and that will inactivate enveloped pathogenic viruses and Gram negative bacteria on contact. Doctors, nurses and other hospital workers need PPE that is effective in preventing the spread of nosocomial infections from patient to patient, as well as being convenient, safe, affordable, disposable, and biodegradable. The fabrics of this invention meet this long felt need and may be used in the production of protective facemasks. The present application incorporates proteases into fabrics that may be used for PPE applications. Specifically this application employs cold active trypsins incorporated into fabrics.

SUMMARY OF THE INVENTION

The invention provides self-sterilizing fabrics incorporating low temperature enzymes, specifically psychrophilic and/or cold active enzymes, which inactivate pathogenic viruses and Gram negative bacteria and prions on contact, including Coronavirus (e.g. Covid19), and Influenza viruses. The fabrics of the invention may be used in the production of protective facemasks and PPE. In a specific preferred embodiments the material incorporates cold active trypsin enzymes derived for organisms that live in cold climates such as (but not limited to) deep sea cod (genus *Gadus*), King crabs (red, particularly), Dungeness, and Snow crabs (also called Tanner crabs).

BRIEF DESCRIPTION OF THE FIGURES

Figure 2:
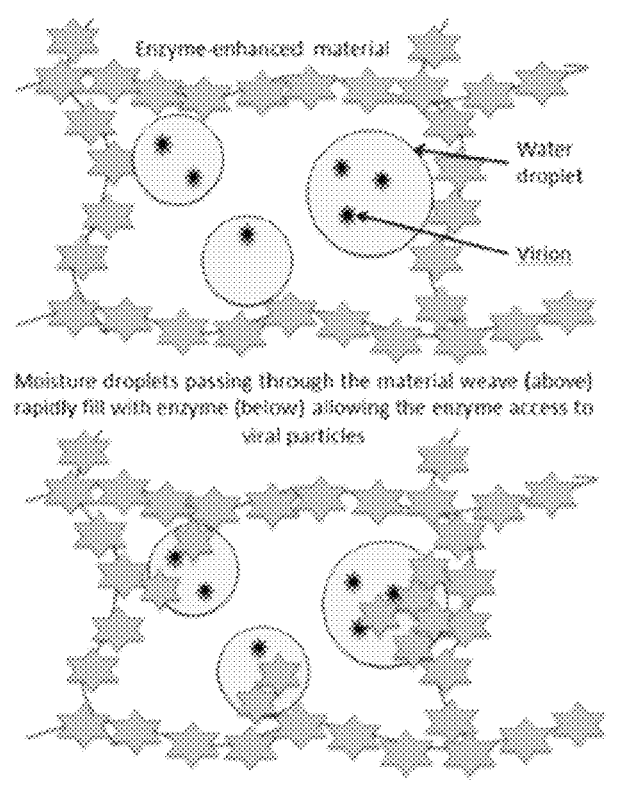

FIG. 2. Schematic diagram showing how activated enzymes disperse into aerosol droplets introduced into the face mask material during breathing (or sneezing, coughing, laughing, etc.).

FIG. 4. A non-exclusive table of enzymes used in the fabrics of the invention.

FIG. 5. Table of commercial enzymes active at low temperature.

DETAILED DESCRIPTION OF THE INVENTION

Figure 1:
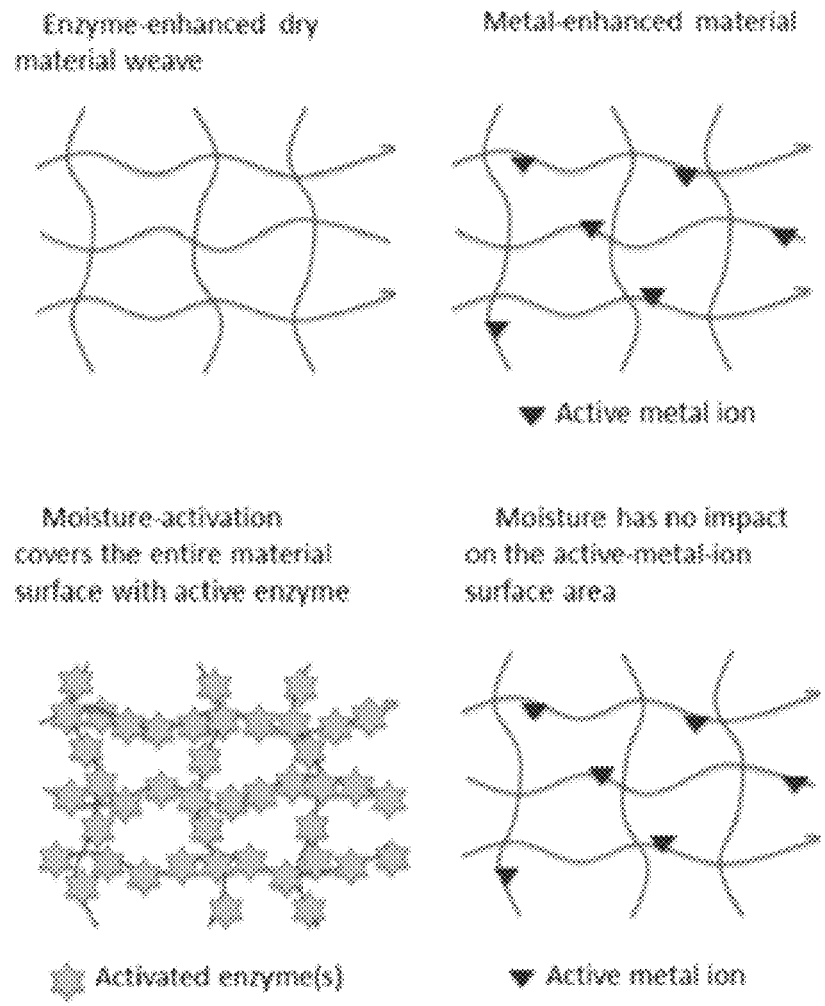
FIG. 1. Schematic diagram showing how moisture activates the enzymes over the entire surface area of the enzyme-enhanced materials, while having no effect on the active surface area of metal-enhanced materials.

The invention provides materials adapted to inactivate enveloped viruses and gram negative bacilli present in an aqueous aerosol upon contact with the material. The material comprises a fabric and a non-specific protease stably incorporated within the fabric. In a preferred embodiment the protease is a psychrophilic protease, active at temperatures below 15 Centigrade. Upon contact with an enveloped virus or a gram negative *bacillus* suspended in aqueous aerosol, the protease in the material inactivates said virus or *bacillus*.

In a preferred embodiment the psychrophilic protease has an activity of at least 0.2 au/hr/ml (where au is absorbance units at 492 nm in an assay that quantifies protease activity using a fluorescein thiocarbamoyl-casein derivative [FTC-derivative] as found in the Calbiochem Protease Assay Kit [Cat No. 539125])X at a temperature of no more than 16° C. In this preferred embodiment, the protease retains at least one-tenth of this activity at 5° C. Note that this data if from the inventors experiment in which 200 microliters of enzyme were put onto a 1 cm square of fabric. The calculated activity was at least 0.04 au/hr/cm2 of fabric.

In a specific preferred embodiment the psychrophilic protease is a Trypsin.

The fabrics, therefore, act as self-sterilizing fabrics for use in PPE applications. Generally, the fabrics can incorporate cold-active non-specific proteases such as psychrophilic and/or cold active trypsin enzymes that inactivate enveloped viral particles such as those of Coronavirus. In some examples the PPE incorporates a psychrophilic and/or cold active protease enzyme only. The proteases are preferably cold active trypsins such as cod trypsins I and ZT.

In some specific embodiments the PPE incorporates a psychrophilic and/or cold active protease that is inactive at temperatures of 37 Centigrade and above. Some may become inactive at temperatures above 30, 32, 35 or 37 Centigrade. In various embodiments the material explicitly does not comprise/contain a lipase enzyme. In various embodiments the material explicitly does not comprise/contain a metal or metal ion. In some examples the material incorporates a psychrophilic and/or cold active protease enzyme as the only enzyme (and in some embodiments may contain no other enzyme types, e.g., no lipases).

In certain embodiments the material incorporates a specific psychrophilic and/or cold active protease enzyme extracted from cod (genus *Gadus*) such as cod trypsins I and ZT or trypsins from crabs such as are found naturally in the hepatopancreas, and can be either extracted from this tissue or made as recombinants. In a specific preferred embodiments the material incorporates cold active trypsin enzymes, and optionally no other types or enzymes except trypsin cold active enzymes.

In other specific embodiments the material incorporates enzymes such as a psychrophilic and/or cold active protease that is inactive at temperatures of 37 Centigrade and above. Some may become inactive at temperatures above 30, 32, 35 or 37 Centigrade. Such enzymes would be inactive if inhaled into the human body, and this would reduce immunogenicity of the proteins if inhaled. On the other hand, humans produce anti-trypsins, so any trypsin that tries to attack human tissue would be inactivated. Alpha-anti-trypsin is present in blood, so a trypsin fabric would not be useful to protect against blood-borne virus (like Ebola).

In a specific embodiment the invention comprises a novel trypsin ZT isoforms as described in US2020/0197288 (Novel trypsin isoforms and their use). US2020/0197288 discloses "unexpected, beneficial and unique characteristics of the novel trypsin ZT isoforms over trypsins known previously." Such isoforms used in the present invention may be selected from the isoforms described in US2020/0197288, for example (i) a trypsin ZT-1, comprising an amino acid sequence according to SEQ ID NO:2; (ii) trypsin ZT-2 comprising an amino acid sequence according to SEQ ID NO:3; (iii) trypsin ZT-3 comprising an amino acid sequence according to SEQ ID NO:4; (iv) and trypsin ZT-4 comprising an amino acid sequence according to SEQ ID NO:5, or a mixture thereof.

For example the inventors are using the red king crab trypsin genes here: Trypsin-1 (Gene ID—TRINITY_DN152101_c5_g1_i2), Trypsin-1 (TRINITY_DN135010_c0_g2_i2), Trypsin-1 (TRINITY_DN140970_c15_g1_i2), Trypsin-2 (TRINITY_DN144602_c7_g1_i1), Trypsin-7 (TRINITY_DN132541_c0_g1_i1). See the Crustacean Annotated Transcriptome Database.

In a further specific embodiment the invention comprises either native trypsin Y or a recombinant form of trypsin Y (described by Palsdottir & Gudmundsdottir, 2007, Protein Expr Purif 51: 243-252, and Palsdottir & Gudmundsdottir, 2008, Food Chemistry 111: 408-414).

Because the enzymes of described in US2020/0197288 are of particular interest to the PPE materials of the present application, and US2020/0197288 does mention the use of the disclosed enzymes in fabric medical devices, the applicants wish to distinguish this art and point out that U/S2020/0197288 in no way discloses or suggests using such enzymes for PPE applications, and specifically does not disclose or suggest the incorporation of the enzymes in or on a fabric for any use. Specifically US2020/0197288 defines the phrase "medical device" as " . . . any instrument, apparatus, appliance, software, material or other article for the purpose of diagnosis, prevention, monitoring, treatment, or alleviation of disease, such as diagnosis, monitoring, treatment, alleviation, of or compensation; for an injury or handicap, such as investigation, replacement or modification of the anatomy or of a physiological process; control of conception; including devices that do not achieve their principal intended action in or on the human body by pharmacological, immunological or metabolic means but may be assisted in their function by such means". This definition does not encompass the embodiments of the present disclosure.

The cold active trypsin enzymes from cod and other species have a very broad temperature range for activity and in some instances provide substantial activity from 4 Centigrade to 55 Centigrade. The activity-temperature range is generally related to specificity, so the broader the temperature range, the lower the specificity of the enzyme. This is beneficial to the current application which preferably uses low-specificity proteases.

Cold-active protease enzymes are produced from many types of psychrophilic and/or cold active organisms including bacteria, fungi, and fish. Psychrophiles or cryophiles are extremophilic organisms that are capable of growth and reproduction in low temperatures, ranging from −20° C. to +10° C. They are found in places that are permanently cold, such as the polar regions and the deep sea. All such enzyme sources are contemplated in this application. Cold-active are generally described as active at or below 20° C., or alternatively, active at or below 15° C., 10° C., 5° C., 4° C. or 2° C. Many are active at 2-5° C.

A major and inexpensive source of cold active trypsin is deep sea cod (genus *Gadus*). Purification of cold active trypsin from cod waste requires only routine enzyme isolation. Another route is to clone the trypsin genes and express them in either *E. coli*, yeast or insect cells using well known commercially available expression vectors and methods.

A specific commercial use of cold adapted enzymes from *Gadus* is ColdZyme® which is a throat spray made by Enzymatica. The product uses an enzyme extracted from deep-sea cod. This cold-adapted trypsin that has evolved to be active at a temperature of around 4° C. This type of enzyme becomes more effective upon exposure to the temperature of the human body, which causes the catalytic activity to be many times higher than in the corresponding human enzyme. Preliminary laboratory tests demonstrate that this product will deactivate about 98.3% of the virus that causes Covid-19. The spray has been available in Iceland for five years and is intended to be used when people feel the first symptoms of a cold. It is marketed and sold commercially and seems to provide no adverse reaction upon application. The formulation contains glycerol, water, cod trypsin, ethanol (<1%), calcium chloride, trometamol and menthol. ColdZyme® Mouth Spray is sold as a 20 ml bottle, pump, spray nozzle and protective cap.

In Stefansson et al. (2017) "A medical device forming a protective barrier that deactivates four major common cold viruses", Virology: Research and Reviews, 1(5):1-3, data is presented for the cod trypsin composition used by Enzymatica. Results of viral deactivation test in Table 1 of the paper show:

Influenza A virus (H3N2)—Percent deactivation 96.9
Respiratory syncytial virus—99.9%
Rhinovirus Type 1A—91.7%
Rhinovirus Type 42—92.8%
Adenovirus Type 2—64.5%

These assays were performed at 35-37° C. for 20 minutes. Exhaled breath has a temperature of about 34° C., which means that on a mask that is being worn, this data is directly relevant. Of course since these are low temperature enzymes, they will also show substantial activity at normal room temperature down to about 5 Centigrade.

A very important regulatory element of the invention is that various trypsins are considered by the FDA to be GRAS (GENERALLY RECOGNIZED AS SAFE). They have been proven to have anti-viral activity and evidence and reasoning suggests that they also inactivate various types of bacteria. In the US trypsins that are used in food preparation are GRAS, for example porcine or bovine mesophilic trypsins; § 184.1914 Trypsin (peptide hydrolase) from porcine or bovine pancreas used to hydrolyze proteins. https://www.fda.gov/food/generally-recognized-safe-gras/enzyme-preparations-used-food-partial-list An important commercial advantage is that they are cheap to source because they can be isolated from marine byproducts.

The enzymes are incorporated within the fabric in such a way that they are stably bound and cannot substantially be released from the fabric and therefore cannot be inhaled by a user. This bonding of the enzymes to the fabric can be achieved by various means including covalent bonding, electrostatic bonding, Van der Wall's forces, bonding by hydrophobic and/or hydrophilic interactions, and other chemical and physical bonding methods.

Alternatively, in certain embodiments that use GRAS proteases, specifically GRAS proteases derived from psychrophiles such as cod or crabs, the enzymes may not be stably incorporated. Such proteases are very stable and safe. Because these enzymes are GRAS, it is desirable that some of the enzyme disassociate from the mask during wear. This is an intentional design feature. This makes the masks more than self-sterilizing because dry enzyme not attached to the mask material can enter droplets of virus-laden fluid that are passing through the holes in the weave. Anti-viral activity of the enzyme will continue even after these droplets have left the mask.

Alternatively the enzymes may be trapped within a layer (or sealed between two layers) of fabric such that the enzyme cannot freely move from the place where it is trapped such that it exits the mask, with consequent risk of inhalation. Electrostatically charged fabrics may be used to trap free enzymes or fragments.

In some typical embodiments the mask has 2 layers, both of which will have enzyme attached or incorporated. The outer layer is more hydrophobic, the inner layer is more hydrophilic. The enzymes can be loosely attached by adsorption. Because these enzymes are GRAS, it is desirable that some of the enzyme disassociate from the mask during wear. This is an intentional design feature. This makes the masks more than self-sterilizing because dry enzyme not attached to the mask material can enter droplets of virus-laden fluid that are passing through the holes in the weave. Anti-viral activity of the enzyme will continue even after these droplets have left the mask.

In certain embodiments the invention provides not a material, but a spray comprising various proteases, specifically the GRAS proteases, specifically GRAS proteases derived from psychrophiles such as cod or crabs. Such proteases are very stable and safe and may be sprayed directly onto any fabric such as a fabric used as a mask, gown, and head covering etc. such as those worn in hospitals and care facilities to reactivate the fabrics anti-viral activity after extended wear or laundering.

Another GRAS mixture that may be used in PPE materials of the invention is a mixed carbohydrase and protease enzyme product derived from *Bacillus licheniformis*. Previously it has been used for hydrolyzing proteins and carbohydrates in the preparation of alcoholic beverages, candy, nutritive sweeteners and protein hydrolysates. But is has characteristics that would make it suitable for digesting and inactivating the glycoprotein spikes on enveloped viruses.

In a preferred embodiment for functionalization, the fabrics of the invention can be functionalized by ozonation, which is a simple and efficient commercial treatment using a plasma.

In another preferred embodiment for functionalization, Corona treatment is used to functionalize the fabrics before addition of enzymes, creating—OH functional groups that the enzyme will bind to.

There are many methods known in the art including those described in "Facile approach to functionalizing polymers with specific chemical groups by an ozone treatment: Preparation of crosslinkable poly(vinylidene fluoride) possessing benzoxazine pendent groups", by Ying-Ling Liu, J. Polymer Science, Volume45, Issue5, 1 Mar. 2007, Pages 949-954. And see Surface Modification of Polymers: Methods and Applications, Chapter 6 Photoinduced Functionalization on Polymer Surfaces, by Kazuhiko Ishihara, Online ISBN: 9783527819249, Print ISBN: 9783527345410. And see UV and ozone treatment of polypropylene and poly(ethylene terephthalate) by Mary Jane Walzak, Journal of Adhesion Science and Technology, Volume 9, 1995—Issue 9, UV and ozone treatment of polypropylene and poly(ethylene terephthalate). And see United States Patent Application 20070009565.

Another important aspect of the present invention is to produce masks that are completely or substantially biodegradable, recyclable, and made from sustainable sources. With billions of polypropylene masks being produced and disposed of every year, they have become a major source of environmental pollution (Oluniyi et al., Sci Total Environ. 2020 Oct. 1; 737:140279). Biodegradability of all the components of the mask is an essential aspect for future mask design. Carbon neutrality of production is also an aim of the present invention, as is sustainability of the source components. Masks that use metals such as copper, zinc and silver are not sustainable, but enzymes provide a sustainable antiviral component. One entirely biodegradable mask embodiment is a bamboo mask optionally coated with chitosan (optionally cross-linked together), with the enzymes adsorbed or covalently attached to the chitosan to make a fully biodegradable mask.

(I) Problems Addressed by the Invention

Disposable facemasks being worn by the general public during the Covid-19 and other pandemics prevent infection by (i) preventing the wearer from touching their face (ii) by removing virus from their expelled breath (iii) to a lesser extent, preventing virus from being breathed in. However, fabrics are fomites, and can act to concentrate, transmit and spread the virus. This is particularly dangerous in a hospital setting where nosocomial infections are a major cause of death. Additionally, the fabric weave of the material used to make these masks leaves sufficient pore space for small, virus-containing droplets, to pass through. There is therefore a need for the efficiency of these masks, that are based on size-exclusion alone, to be improved, particularly during inhalation.

(II) What are the Currently Used Solutions that Address this Problem?

Disposable "surgical" facemasks of the type worn by the public (i.e. non-N95 masks), are meant to filter out virus by size exclusion. While the SARS-CoV-2 virus is 120 nm (0.12 microns) in diameter, such viral particles do not exist in an environmental sense as individual particles, but are carried in water droplets with a range of much larger sizes. Aerosolized viruses are carried in aqueous micro-droplets and are classified by WHO as droplet (>5 μm) or airborne (<5 μm) transmission. Only the largest particles are removed by the current "surgical" masks. Reducing the pore size of the masks provides one method of increasing viral filtration efficiency. N95 masks have a filtering ability down to between 0.3 and 0.1 microns (depending on the manufacturer's claims) and are said to filter out particles with such a diameter with 95% efficiency.

Home-made fabric masks have become popular, and they have the advantage of being washable and reusable, but of course their filtration efficiency entirely depends on their design and the fabric used, and unless washed, they act as fomites.

Some currently available facemasks incorporate copper or silver or zinc metals. Interaction with a solid copper surface has been shown to inactivate virus particles after several hours. These facemasks are marketed as 'anti-microbial'. Any killing effect that is theoretically possible is only provided on contact with the metal, and the vast majority of the surface area of such masks does not incorporate an effective proportion of metal ions. Making these masks anti-viral using this approach would require adding a proportion of metal to the material that would make the mask both extremely uncomfortable to wear and prohibitively expensive. Consequently, this solution is impractical. Additionally they use a non-sustainable material (metals extracted by mining being a non-renewable resource) which causes environmental harm.

(III) What are the Shortcomings/Disadvantages of the Current Solutions?

The main shortcoming of the present masks is their activity as fomites. Disposable face masks do a good job of concentrating particles on their outside, increasing the probability of introduction of an infectious dose to the user if they then touch their nose, mouth or eyes. Wearers have a tendency to touch, adjust, partially remove or fully remove the mask. Users do this because masks become uncomfortable, hot and moist and itchy. Adjusting the mask reduces any seal effect and allows air to flow directly round the mask into the mouth or nose. Additionally touching the mask transfers the concentrated particles from the outside of the mask to the fingers of the user, increasing the probability of introduction of an infectious dose to the user if they then touch their nose, mouth or eyes. Thus masks inherently act to spread viruses and bacteria carried on their surfaces and act as ideal fomites.

Some disposable facemasks are marketed as anti-microbial. These masks contain metals, such as silver or copper. However, the addition of metals to these masks does not add significant anti-viral properties. The metals prevent the growth of bacteria and fungi, thereby extending their lifetime. The metals have not been shown to kill virus lodged in the mask material. Adding an efficient anti-viral component to disposable facemasks would improve their efficiency and efficacy in preventing viral infections.

Copper and silver-containing anti-microbial facemasks currently being produced reduce growth of bacteria and fungi in the mask material, thereby reducing odors and extending the length of time an individual mask can be worn. However there are many disadvantages to these masks. The killing effect is only provided on contact with the metal, and the vast majority of the surface area of such masks does not incorporate an effective proportion of metal atoms/ions. Making these masks anti-viral using this approach would require adding a proportion of metal to the material that would make the mask both extremely uncomfortable to wear and prohibitively expensive. Consequently, this solution is impractical. Additionally cost and non-sustainability make them a poor choice for PPE. Advantages over metal-containing masks are specifically addressed by the present invention as illustrated in FIGS. 6 and 7. The present invention has particular advantages over metal-containing masks. Moisture activates the enzymes over the entire surface area of the enzyme-enhanced materials, while having no effect on the active surface area of metal-enhanced materials. Activated enzymes disperse into aerosol droplets introduced into the face mask material during breathing (or sneezing, coughing, laughing, etc.)

Another problem is environmental impact of the disposal of billions of polypropylene masks. They cause significant environmental damage.

None of the present mask designs provide low price, convenience, safety & effectiveness with sustainability and biodegradability.

(IV) What is the New Solution and how does it Address the Current Problems?

The aim of this invention is to enhance the efficiency and efficacy of disposable materials such as facemasks in preventing viral infection and reduce fomite-mediated transmission by incorporating virus-degrading enzymes into the mask material. The enzymes will degrade virus particles carried in aqueous micro-droplets passing through the mask and inactivate virus lodged in the mask material, thereby reducing infections based on wearers transferring virus from their masks to their hands and faces when the mask is worn or touched during removal, repositioning or pocketing. The fabrics of the invention provide a self-sterilizing material which in public use will reduce disease transmission and in health-care environments should significantly reduce nosocomial infection—a major cause of death.

Biodegradability and carbon neutrality of production is an aim of the present invention, as is sustainability of the source components. Masks that use metals such as copper, zinc and silver are not sustainable, but enzymes provide a sustainable antiviral component. Some embodiments of the fabrics/masks of the present invention are completely or substantially biodegradable, recyclable, and made from sustainable sources.

The surface of enveloped viruses, such as influenza and coronaviruses is composed of lipids and proteins. Both types of biological material are susceptible to attack by enzymes. Lipids are degraded by lipases while proteins are degraded by proteases.

The surfaces of non-enveloped viral particles are composed of proteins and glycoproteins, which are likewise susceptible to degradation by the enzymes disclosed in the present invention.

The laundry detergent industry has for many years incorporated biological enzymes into dry laundry powders and stain removers. Enzymes are also routinely lyophilized (i.e. stored in a dry format). The enzymes are re-activated by the addition of water. Enzymes immobilized on dry fabrics would likewise be re-activated by the addition of water in the format of respiratory droplets.

We propose incorporate proteases into the material of disposable facemasks to enhance their ability to prevent viral infections including those caused by influenza viruses and Coronaviruses such as Covid-19.

Proteases used in detergents and the food industry are often non-specific serine endoproteases that cleave on the hydroxyl-side of the hydrophobic amino acid residue. These enzymes are non-specific in that they are capable of hydrolyzing most peptide links.

Other proteases, not currently used in detergents (e.g. thiol proteases or metalloproteases), may also prove useful in anti-viral facemasks.

Consequently, enzymes that have been selected for use in the detergent or food industry may prove ideal for incorporation into facemask material because they are broadly active, work at temperatures below body temperature, and are produced inexpensively in extremely large quantities. They have also been thoroughly tested for dermatologic tolerance.

Proteases and other enzymes which may be used in the present invention are listed in the paper by Hasan et al., *Enzymes used in detergents* August 2010 AFRICAN JOURNAL OF BIOTECHNOLOGY 9(31) which is hereby incorporated by reference for all purposes.

The enzymes present in these new anti-viral facemasks are activated when droplets of water touch the facemask material. The enzymes are solubilized under these conditions and move throughout the droplets.

This enzymatic anti-viral approach is superior to using metals in facemasks because of this solubility effect. Additional advantages are those of effectiveness and cost. The enzymes work extremely quickly and do not require hours of exposure, unlike copper/silver impregnation. The enzyme-impregnated mask is both easy to manufacture and cheaper to produce than the metal-impregnated design.

To the inventors' knowledge, detergent or food-industry enzymes have never been incorporated into facemasks, or other PPE materials, to make use of their anti-viral properties. This approach to improving the efficiency of facemasks to prevent the spread of diseases, such as Covid-19, is consequently totally novel.

The invention is capable of being used to inactivate not only organisms transmitted by droplets, but any organism that comes in contact with the fabrics of the invention such that enzymes are solubilized in an aqueous (or micro-aqueous) solution.

Enzyme-incorporating masks are suitable for the prevention and reduction in transmission of any viral respiratory diseases. These include (non-exclusively): influenza, the common cold, respiratory syncytial virus infection, adenovirus infection, parainfluenza virus infection, severe acute respiratory syndrome (SARS) and Covid19. Enzyme-incorporating masks may also be suitable for the prevention and reduction in transmission of any bacterial diseases, including, but not limited to *Escherichia coli, Pseudomonas aeruginosa, Chlamydia trachomatis, Yersinia pestis*, and species of *Bartonella, Brucella, Coxiella, Leptospira, Rickettsia, Ehrlichia*, and *Chlamydia*. Gram negative bacteria may be particularly susceptible to the fabrics of the invention. Target organisms may include airborne organisms spread by droplet transmission such as coronaviruses and influenza, *legionella*, mycobacteria, prions etc. It may include organisms responsible for Pneumonia, such as bacteria or viruses, and less commonly fungi and parasites. Pneumonia-causing bacteria most commonly (50% of cases) include *Streptococcus pneumonia*, but also include *Haemophilus influenza* (20%) *Chlamydophila pneumoniae* (13%) and *Mycoplasma pneumoniae* (3%), *Staphylococcus aureus, Moraxella catarrhalis*, and *Legionella pneumophila*. Viruses that would be susceptible to the invention include, for example, rhinoviruses, coronaviruses, influenza virus, respiratory syncytial virus (RSV), adenovirus, and parainfluenza viruses. Fungi that would be susceptible to the invention include, for example, *Histoplasma capsulatum, Blastomyces, Cryptococcus neoformans, Pneumocystis jiroveci* (*pneumocystis* pneumonia, or PCP), and *Coccidioides immitis*. Parasites that would be susceptible to the invention include, for example, *Toxoplasma gondii, Strongyloides stercoralis, Ascaris lumbricoides*, and *Plasmodium*

*malariae*. These organisms typically enter the body through direct contact with the skin, ingestion, or via an insect vector. Because humans produce anti-trypsins, a trypsin based anti-viral will not work on microbes introduced into blood by bites. It will also not work on healthy skin tissue, hence why it can be used for debridement, it only removes dead tissue. Trypsins can really only be used for respiratory pathogens. Except for *Paragonimus westermani*, most parasites do not specifically affect the lungs but involve the lungs secondarily to other sites. Gram negative pathogens such as *Escherichia coli, Pseudomonas aeruginosa, Chlamydia trachomatis*, and *Yersinia pestis* would also be susceptible to the invention.

Various Embodiments of the Invention

Embodiments are not limited to masks, but encompass all fabrics and related materials that are impregnated with or sprayed with enzymes that have anti-viral, anti-bacterial, or anti-microbial activity. The invention includes fabrics into which proteases and/or lipases are stably incorporated.

In certain embodiments, more than one protease, and/or more than one lipase are incorporated into the fabric. This can be beneficial so that enzymes with different temperature-dependent spectra of activity can be incorporated into a single fabric, allowing sufficient antiviral activity over a broad range of temperatures. Enzymes with overlapping temperature-dependent activities can be used in the same fabric.

Apart from lipases and proteases, certain other enzymes may be incorporated into the fabrics of the invention such as enzymes that degrade glycoproteins such as glycosidases, and aspartyl-glucosaminidase or enzymes that degrade lipids such as lipases.

In one embodiment, the invention encompasses fabrics and similar materials into which proteases only are stably incorporated. In one embodiment, the invention encompasses fabrics and similar materials into which lipases only are stably incorporated. In one embodiment, the invention encompasses fabrics and similar materials that are stably impregnated with or sprayed with both proteases and lipases. In general embodiments, the proteases used in the invention are non-specific serine endoproteases. These are capable of hydrolyzing most peptide links (FIG. 4).

The proteases used in the invention generally have low substrate specificity, work well at room temperatures, and are stable in the presence of other proteases or at high concentrations of themselves (because of a lack of accessible digestion sites in the enzyme). Many commercial proteases are known that work at low temperature. See D. Kumar et al., 2008. *Microbial Proteases and Application as Laundry Detergent Additive*. Research Journal of Microbiology, 3: 661-672, incorporated by reference herein for all purposes. Crustacean enzymes are particularly stable with respect to self-digestion (See Hehemann et al 2008 *Autoproteolytic stability of a trypsin from the marine crab Cancer pagurus*. Biochemical and Biophysical Research Communications, 370: 566-571.)

In some embodiments, proteases may be, for example endoproteases or exoproteases, cutting at any amino acid at any location, and may be specific or non-specific in their action. A typical example used in the invention is a serine endoproteases such as trypsins. Proteases used in the invention may include, alone or in combination, for example, and non-exclusively, Serine proteases, Cysteine proteases, Aspartic proteases and Metalloproteases. Subtilisins produced from fermentation of *Bacillus licheniformis* are often used in cold acting detergents. Two proteases used in cold washing detergent are Subtilisin Carlsberg, and Subtilopeptidase A. In other embodiments, thiol proteases or metalloproteases may be used. Other embodiments may employ proteases selected from one or more of (alone or in any combination) Trypsin, Chymotrypsin, Endoproteinase Asp-N, Endoproteinase Arg-C, Endoproteinase Glu-C, Endoproteinase Lys-C, Thermolysin, Elastase, Papain, Proteinase K, Subtilisin, Clostripain, Exopeptidase, Carboxypeptidase A, Carboxypeptidase P, Carboxypeptidase Y, Cathepsin C, Acyl-amino-acid-releasing enzyme, and Pyroglutamate aminopeptidase.

Crustaceans produce particularly stable protease enzymes. See Ref. Hehemann et al 2008 Autoproteolytic stability of a trypsin from the marine crab Cancer pagurus. Biochem. Biophys. Res. Comm. 370:566-571. Crab trypsin retains 60% activity after 21 days at room temperature in liquid. This is very stable in dried form.

In various embodiments we may use and enzyme mixture comprising a blend of cold-adapted trypsins with overlapping activity profiles to cover a range of temperatures. See Gudmundsdottir et al (2013) Potential use of atlantic cod trypsin in biomedicine, BioMed Res International. Cold-adapted trypsins from cod are between 3 and 12 times more efficient than a mesophilic trypsin (bovine) at degrading a range of proteins. The Gudmundsdottir studies were performed at 4° C., 25° C., and 37° C., and enzymes do remain active above these temperatures. Adsorption to a fabric could increase the maximum temperature of the enzyme.

One possible enzyme blend could be created from a non-purified slurry of crab extract. This would provide a very inexpensive enzyme formulation making the technology available at low cost. Alternatively simple chemical extractions may be performed for an extract.

Figure 3:
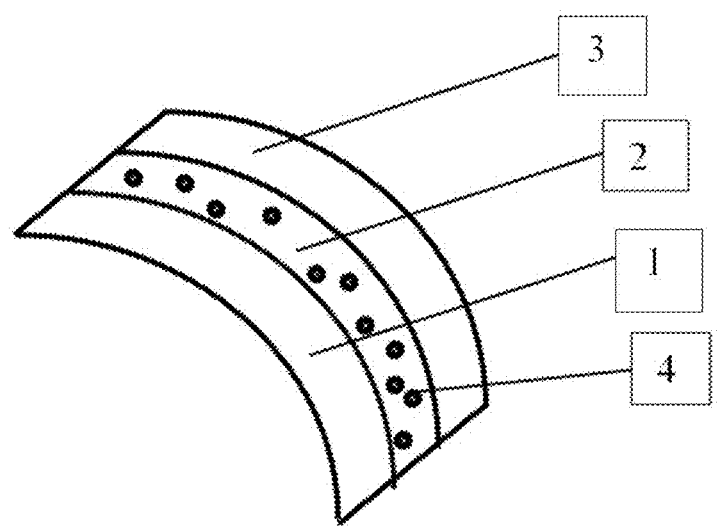
FIG. 3. Schematic diagram of an embodiment of the invention comprising three layers of fabric, as used in a face-mask, 1=inner layer nearest to user's face; 2=middle layer impregnated with enzymes; 3=outer layer with greater porosity than second layer; 4=enzymes incorporated into fabric.

Commercial detergents containing proteases and lipases have been used for years. Various lipases that are used in detergents and may be used in the present invention are discussed in D'Souza N M, Mawson A J (2005). "Membrane cleaning in the dairy industry: A review. Crit. Rev. Food Sci. Nutr. 45: 125-13. Lipases, in general embodiments of the invention, act as esterases (FIG. 3). In general embodiments, the lipases used in the invention have low substrate specificity, work well at room temperatures and are stable in the presence of proteases.

In general embodiments, the lipases convert triglyceride substrates to monoglycerides and two fatty acids. Lipases used in the invention will generally need to be active at lower temperatures, such as room temperature, between 5 or 10 and 25 or 30 degrees Centigrade. Cold active lipases (CLPs) are preferably used because they exhibit high catalytic activity at low temperatures. Since they are active at low temperatures consume less energy and also stabilize fragile compounds in the reaction medium. CLPs are commonly obtained from psychrophilic and/or cold active microorganisms which thrive in cold habitats. CLPs include *C. antarctica* lipase-A and *C. antarctica* lipase-B from *Candida antarctica* isolated from Antarctic organisms. These are well studied and industrially employed. See Cold active lipases—an update, M. Kavitha Frontiers in Life Science, 2016 VOL. 9, NO. 3, 226-238, incorporated herein by reference for all purposes. In other embodiments, lipases may be, for example (non-exclusively), Lipolase (Novo Nordisk, Denmark), Lumafast (Genencore, USA), or Lipofast (Advanced Biochemicals, India).

In this invention, we may use the terms psychrophilic and/or cold active enzymes, as differentiated from the broader group of simply "cold-adapted" enzymes.

In the present disclosure we may define the psychrophilic proteases of the invention as proteases that are active to at least 0.04 au/hr/cm² at temperatures below 16° C. We may say that a protease X has an activity of Y at a temperature Z.

When attached to bamboo fabric by adsorption, Atlantic cod trypsin I had an activity of at least 0.04 au/hr/cm2 at 16° C., and an activity of at least 0.1 au/hr/cm2 at 37° C. (where au is absorbance units at 492 nm, a proxy for protease activity based on the enzymes ability to cleave fluorescein thiocarbamoyl-casein [FTC-casein], as in Twining, S. 1984 Anal Biochem 143: 30).

Psychrophiles or cryophiles are extremophilic organisms that are capable of growth and reproduction in low temperatures, ranging from −20° C. to +10° C. They are found in places that are permanently cold, such as the polar regions and the deep sea. A psychrophile is defined as an organism living permanently at temperatures close to the freezing point of water, in thermal equilibrium with the medium, this definition encompasses a large range of species from Bacteria, Archaea, and Eukaryotes. This aspect underlines that psychrophiles are numerous, taxonomically diverse, and have a widespread distribution. In these organisms, low temperatures are essential for sustained cell metabolism. Some psychrophilic and/or cold active bacteria grown at 4° C. have doubling times close to that of *Escherichia coli* at 37° C. See Roulling F., Piette F., Cipolla A., Struvay C., Feller G. (2011) Psychrophilic and/or cold active Enzymes: Cool Responses to Chilly Problems. In: Horikoshi K. (eds) Extremophiles Handbook. Springer, Tokyo.

Additional components can include enzyme cofactors, such as calcium salts/ions ($Ca^{2+}$). Some enzymes require $Ca^{2+}$ (and sometimes other divalent cations such as $Mg^{2+}$) for thermal stability and/or catalytic activity. Calcium may be required for the full activity of many enzymes, such as protein phosphatases, and adenylate kinase. In some instances it activates enzymes in allosteric regulation. Other cofactors may include salts/ions of iron, magnesium, manganese, cobalt, copper, zinc, and molybdenum.

Other non-enzymatic components that can also be incorporated into the fabrics of some of the embodiments include polyphenols. Some polyphenols have been shown to inhibit RNA-dependent RNA polymerase (RdRp). Such polyphenols include EGCG, theaflavin (TF1), theaflavin-3'-O-gallate (TF2a), theaflavin-3'-gallate (TF2b), theaflavin 3,3'-digallate (TF3), hesperidin, quercetagetin, and myricetin, which all strongly bind to the active site of RdRp.

Other non-enzymatic components that can also be incorporated into the fabrics of some of the embodiments include citrate and other organic acids and salts thereof and other organic acids and components.

In some embodiments, salts may be added such as sodium chloride, calcium chloride, potassium chloride, sodium citrate, etc. These salts may have antiviral properties as well as anti-bacterial properties. Enveloped viruses and gram negative bacilli are inactivated by salts. Because salts may interfere with enzymatic activity they may be incorporated into parts or layers of the mask separate from the parts that contain the enzymes. As separate layer may be incorporated into a mask layer either in front (distal to the user) of or behind (proximal to the user) the enzyme layer.

Although on the fringes of western pharmaceutical sciences, there are a number of very interesting traditional Chinese medicines that have been used for many decades if not for centuries, that now appear to show promising antiviral activity. A recent in silico study has identified a number of interesting candidates. One or more of these herbal may be incorporated on or into the fabric of the invention, for example into at least one layer of the masks of the invention. See: Denghai Zhang et al., Journal of Integrative Medicine; Volume 18, Issue 2, March 2020, Pages 152-158*, In silico screening of Chinese herbal medicines with the potential to directly inhibit* 2019 *novel coronavirus*; incorporated by reference. This 2020 study's aim was to execute a rational screen to identify Chinese medical herbs that are commonly used in treating viral respiratory infections and also contain compounds that might directly inhibit 2019 novel coronavirus (2019-nCoV). Natural Chinese medical herbal products that may be used include the following: *Forsythia suspensa* (weeping forsythia); *Glycyrrhiza glabra* (liquorice); *Tussilago farfara* (colsfoot); *Morus alba* (black mulberry); *Chrysanthemum* flower; *Lonicera japonicae* (Japanese honeysuckle); *Peucedanum praeruptorum* (hog fennel); *Fagopyri cymosi* (wild buckwheat); *Tamarix chinensis* or *cacumen* (Chinese tamarisk); *Erigeron breviscapus* (fleabane); *Bupleurum chinense* (thorowax); *Coptis chinensis* (goldthread); *Houttuynia cordata* (fish mint) leaf; *Hoveniae dulcis* (Japanese raisin tree) seed; *Inula helenium* or *japonica* (Elecampane) flower; *Eriobotrya japonica* (loquat); *Hedysarum multijugum* (sweetvech) leaf; *Lepidium* (pepperweed) seed; *Ardisia japonica* (marlberry) leaf; *Aster tataricus* (Tatarinow's *Aster*); *Euphorbia helioscopia*; (madwoman's milk); *Gingko biloba* seed; *Anemarrhena asphodeloides* (zhi mu) root; *Epimedium sagittatum* (bishop's hat) and *Dryopteris crassirhizoma* (shield fern).

Traditional Chinese Medicines have proven to be a valuable source of antiviral, antibacterial, anti-inflammatory and antioxidant compounds (Chen and Yu, 1999), for example, the TCM "Shuanghuanglian" has been used as an antiviral and antibiotic drug to treat respiratory-related diseases in China since 1973 (Zhang et al., 2013), its chemical components include chlorogenic acid, baicalin, and forsythia glycosides (Zhang et al., 2013); "Artemisinin" has been famous for its anti-malaria activity since 1979 (Tu, 2011). The discoverer Youyou Tu was awarded the Nobel Prize for Physiology or Medicine in 2015 (Su and Miller, 2015). These compounds have various antiviral and immune-modulatory effects (Duan et al., 2015; Ge et al., 2018).

Also see Bello-Onaghise G, Wang G, Han X, Nsabimana E, Cui W, Yu F, Zhang Y, Wang L, Li Z, Cai X, Li Y. Antiviral Strategies of Chinese Herbal Medicine Against PRRSV Infection. Front Microbiol. 2020 Jul. 28; 11:1756. doi: 10.3389/fmicb.2020.01756. PMID: 32849384; PMCID: PMC7401453; incorporated by reference.

Another embodiment is an Anti-prion fabric with just cold-adapted (preferably psychrophilic and/or cold active) proteases either adsorbed to the fabric material or covalently attached to it. This is a 3-ply mask with the protease layer in the middle.

Another embodiment is an antiviral fabric with allylamine functionalization of both middle and inner fabric layers: It provides an antiviral face mask with cold-adapted (preferably psychrophilic and/or cold active) proteases and lipases in the middle filter layer along with 2% citrate. The middle layer may be made of PP functionalized with allylamine gas to have a positively charged surface (amine groups). The enzymes, which are slightly negatively charged would then adsorb to this surface. The inner PP fabric would also be functionalized with allylamine and be covered in positive charge so that any enzyme breaking off the middle layer would be attracted to and adsorbed by the inner mask layer and not pass through this layer. In a related embodiment, however, using trypsins negates this requirement. In certain embodiments it is desirable for enzymes to break off and float around in the mask, and even be breathed in by the wearer, giving the enzymes more access to the virus.

Another embodiment encompasses the use of food industry enzymes. These are cold adapted proteases used in the food industry due to the fact that they are thermally unstable at higher temperatures, and can be selectively and rapidly inactivated when required. Their role is to tenderize meat and release amino acids that add flavor. Where laundry detergent enzymes are used in any embodiment, we could equally use food industry enzymes. Cold-adapted or psychrophilic and/or cold active or psychrotolerant enzymes may all be used.

Anti-microbial mask with chitosan and enzymes: An anti-microbial face mask using fabric that has been covered in chitosan which has well known anti-microbial activity due to its polycationic nature. The positive charge on the chitosan is caused by amine groups. These amine groups could be used to adsorb cold-adapted enzymes onto the fabric surface. Chitosan can be cross-linked to cotton using dimethylol dihydroxy ethylene urea (DMDHEU), polycarboxylic acids (1,2,3,4,-butane tetra carboxylic acid and citric acid—Alonzo et al 2009) or derivatives of imidazolidinone (Huang et al 2008). Cross linking occurs through hydroxyl groups. Alonzo et al 2009 Carbohydrate Polymers 77(3): 536-543. Huang et al 2008 Carbohydrate Polymers 73(2): 254-260

The invention provides fabrics that incorporate enzymes that inactivate viral particles, particularly enveloped viral particles such as those of Influenza virus and Coronavirus (e.g. Covid-19). The fabrics of the invention may be used in the production of various items including protective facemasks.

The fabrics of the invention work to inactivate not only viruses, but any microorganism that comes in contact with them that is susceptible to proteases and lipases or other relevant enzymes. Thus the invention is well suited to the inactivation of any organism that may come in contact with them. The fabrics of the invention may be used to inactivate not only organisms transmitted by droplets, but any organism that comes in contact with the fabrics of the invention in such a way that enzymes are solubilized in an aqueous (or micro-aqueous) solution.

The enzymes may be incorporated into a fabric by impregnating, spraying or soaking the fabric with a solution containing the enzyme(s).

Fabrics include spun, woven or non-woven or knitted, printed or pulped-and-dried materials regardless of flexibility or plasticity; for example, fabrics include (non-exclusively) all forms of paper fabric, chitosan, cotton, wool, jute, hessian, linen, soy, silk as well as man-made fabrics such as polyester, rayon, carbon fiber etc. and blends of man-made and natural materials.

Masks of the invention may be multi-layered. It may be advantageous to have different layers that have different functions and/or that incorporate different components. So it is important to understand when reading this disclosure that certain combinations of components may be used together but incorporated into different parts, areas, regions or layers of the mask/PPE. This may be especially important when certain components would interfere with functionality of other components if they were in contact. For example, salts or citrate may interfere with enzyme activity or polyphenol activity.

Enzymes incorporated into the fabric include proteases and lipases. Proteases are generally non-specific proteases, cutting any amino acid at any location, being either endo-proteases or exoproteases. A typical example of a protease used in the invention is a serine endoprotease. Any lipase may be used such as Cold active lipases.

The enzymes of the present invention must be functionally active at room temperature for example at or below 15° C. to 25° C. and above, preferably between 17° C. to 23° C. Other ranges may be, for example, from 0° C. to 40° C., from 5° C. to 35° C., from 7° C. to 30° C., from 10° C. to 25° C. or from 10° C. to 27° C. The degree of efficiency in use, at these temperatures provides an inactivation value $T_{90}$ between 30 seconds and 60 minutes, more specifically up to 45 minutes or up to 30 minutes or up to 15 minutes. Such a $T_{90}$ can be measured using the non-pathogenic enveloped bacteriophage Phi6 ($\phi$6) as a surrogate for enveloped viruses. Other test viruses include *Escherichia* virus MS2 or bacteriophage f2, bacteriophage Qβ, R17, and GA. Other pseudotypes that can be used include those derived from HIV, influenza etc. and of course coronaviruses.

The invention provides fabrics that incorporate enzymes that inactivate pathogens such as viral particles or any type of microorganism susceptible to the enzymes used. The target pathogens are inactivated upon contact with the fabric in the presence of moisture, which solubilizes the enzymes and makes them active. Moisture is generally provided by the fluid in which the pathogens are suspended. This may be aqueous particles exhales from the respiratory system or coughed or sneezed out via the lungs, larynx, pharynx or indeed derived from and expelled from the esophagus. The moisture may also be provided by any pathogen-containing body fluids such as blood, serum, sputum or any other fluid from any animal or indeed any plant.

PPE embodiments include all fabrics and uses of fabrics that may be used in a hospital or healthcare setting or a domestic setting where reduction in transmission pathogens is desirable. The invention is particularly well suited to producing disposable, single-use, anti-microbial fabrics, such as woven (or non-woven) paper fabrics for use as masks, paper tissues, bed clothes, pillowcases, curtains, gowns, clothes, head-coverings, surgical-ware, napkins, sanitary and absorbent coverings etc. and disposable clothes used in food-production and food-processing and in animal husbandry and agricultural processing settings.

Embodiments also include all fabric filters. Filters include those used for any purpose including filtering air, water, and any liquid or fluid. Filters may be used in air handling and air conditioning and air filtration systems. Filters may be used in air filtration systems in buildings and in cars, trains, airplanes and other vehicles. Such filtration systems would require a source of moisture to activate the enzymes.

The fabrics have the additional advantage of being incinerateable to produce no toxic byproducts, and also biodegradable. Additionally they may be made from recycled paper pulp. Additionally they have the advantage of being very easy and inexpensive to produce since all the components are readily available in every continent, and cheap and easy to produce.

Most of the embodiments above disclose fabrics/masks in which the enzymes are either distributed within the fabric or sprayed onto the fabric, and we do not mention the layered structure of the mask material. However, many masks are made of more than two layers of paper (typically three layers; FIG. 5). In certain embodiments, in use, (that is to say in the manufactured item), the items made from the materials comprise at least two layers. Sometimes all layers will comprise the enzyme(s).

In PPE masks of the invention, sometimes less than all layers will comprise the enzyme(s). This may be useful in an embodiment where it is desirable to keep the enzyme-impregnated layer away from the skin. For example, in a face mask made from 3 layers, only the middle layer may be enzyme-impregnated/sprayed such that the layer nearest the skin does not include enzymes. Or in a face mask made from 3 layers, or made from 2 layers, only the outer layer may be enzyme-impregnated/sprayed. This may be a preferred embodiment.

Or in another face mask made from 3 layers, only the middle layer may be enzyme-impregnated/sprayed. Three layers may be present and the outer layer may be more porous than the middle or inner layers. That is to say that the outer layer will allow larger particles to pass through than the middle layer or the inner layer. Droplets carrying pathogens will pass through the outer layer and be trapped in the enzyme-impregnated middle layer, and inactivated. This may be a preferred embodiment.

In other embodiments different layers may include different components to perform different functions. A separate layer may be incorporated into a mask layer either in front (distal to the user) or behind (proximal to the user) the enzyme layer.

Additional components can include enzyme cofactors, such as calcium salts/ions ($Ca^{2+}$). Some enzymes require $Ca^{2+}$ (and sometimes other divalent cations such as $Mg^{2+}$) for thermal stability and/or catalytic activity.

Layers may include polyphenols, such as EGCG, theaflavin (TF1), theaflavin-3'-O-gallate (TF2a), theaflavin-3'-gallate (TF2b), theaflavin 3,3'-digallate (TF3), hesperidin, quercetagetin, and myricetin.

Other embodiments can include citrate and other organic acids and salts thereof, sodium chloride, calcium chloride, potassium chloride, sodium citrate, etc.

Others may incorporate traditional Chinese medicines such as those discussed in Denghai Zhang et al., Journal of Integrative Medicine; Volume 18, Issue 2, March 2020, Pages 152-158, In silico screening of Chinese herbal medicines with the potential to directly inhibit 2019 novel coronavirus.

These embodiments that include separate and additional layers incorporating one or more of the non-enzymatic components mentioned herein, these layers may explicitly exclude enzymes.

A specific commercial embodiment of the invention comprises a disposable face mask which when worn, covers the nose and mouth of a wearer, comprising at least two layers of fabric, wherein one layer of fabric has enzymes incorporated within it, and comprise low-temperature proteases and low-temperature lipases, which enzymes are functionally active at a temperature between 17° C. to 23° C., and wherein, the fabric layer that has enzymes incorporated within it is separated from the face of the wearer by at least one other layer of fabric that does not have enzymes incorporated within it wherein the enzymes inactivate enveloped viruses carried in an aqueous droplet, upon contact with the fabric, wherein the inactivation time $T_{75}$ is less than 30 minutes.

Some embodiments explicitly exclude enzymes that bind specifically to the spike protein of a coronavirus. The enzymes used in the invention may bind to and degrade the spike proteins, but they will not bind specifically, that is to say they will not bind with substantially greater binding affinity to the spike protein of coronavirus than they would to another viral spike protein or other similar protein. Generally they are referred to as non-specific proteases and enzymes.

A preferred specific commercial embodiment of the invention comprises a face mask described above comprising at least three or more layers of fabric, wherein an outer layer (the third layer) is positioned on the outer surface of the second layer (the enzyme-impregnated layer) forming a permeable barrier between the environment and the second layer, and wherein the third layer is adapted to allow the free passage of larger diameter air-borne aqueous droplets than is the second layer, such that some air-borne aqueous droplets which pass through the third layer are adsorbed onto the second layer, such that the droplets, when adsorbed onto the second layer, solubilize and activate the enzymes in the second layer.

This last mask embodiment is particularly effective as it both traps and destroys viral pathogens while keeping them sequestered from the outer surface of the mask. This makes the masks more sanitary and more effective in use, and reduces the probability of user contamination.

Electret fabrics may be incorporated into a separate layer such that the electret layer does not incorporate enzymes and specifically excludes enzymes.

A further embodiment specifically designs around other face-masks from the University of Kentucky (UK) that incorporate proteases that bind specifically to coronavirus spike proteins. There are several potential difficulties and disadvantages in the UK design. Firstly, these are enzymes that bind specifically to the spike-protein. These enzymes are not commercially available easily or cheaply or in large quantities. They must be created and manufactured by complex and expensive biological processes. This contrasts with the enzymes (proteases and lipases) of the present invention which have been developed over many years for use in washing detergents. They are cheap, well-researched and dermatologically tested. Secondly, the University of Kentucky mask, when in use, will not necessarily create an appropriate chemical and osmotic environment for the proteases to adopt the correct confirmation that will be required for enzyme activity. Thirdly the University of Kentucky (UK) mask only uses specific protease enzymes that bind only to the coronavirus spike protein. It does not employ non-specific enzymes, and it does not comprise lipases or other enzymes or multi-enzyme blends as does the present invention. Fourth, the enzymes used in the UK mask are not and have not been designed to be active at low temperatures, such as at room temperatures, for example 10-20 degrees centigrade. Therefore they will not function efficiently as room temperatures.

The prior art masks do not comprise non-specific or low specificity enzymes; they do not comprise enzymes designed to be active at low temperatures or enzymes that have the $T_{90}$ of the present invention. There is no reason to believe that a person could successfully use these prior art inventions to produce the invention of this disclosure (i.e., no expectation of success). They do not comprise a blend of low-temperature enzymes comprising proteases and lipases and the enzymes are not designed to be stable at low temperatures or incorporated into fabrics in a dried form.

Some embodiments of the present invention specifically exclude certain types of enzymes, for example enzymes that bind specifically to the spike protein (or any other protein) of a coronavirus (or any other type of virus), but bind less well and with less specificity to most other proteins that do not have a structure similar to that of the spike protein. Some of the embodiments of the invention comprise only non-specific or low-specificity enzymes. Such protease enzymes may bind at least as well to common proteins such as Casein as they do to a coronavirus spike protein.

For example the invention may specifically exclude enzymes that bind specifically to the spike protein of a coronavirus, but specifically include psychrophilic trypsins, Serine proteases, Cysteine proteases, Aspartic proteases and/or Metalloproteases and also comprise Cold active lipases (CLPs), such as *C. antarctica* lipase-A and/or *C. antarctica* lipase-B from *Candida Antarctica*.

They may alternatively specifically exclude enzymes that bind specifically to the spike protein of a coronavirus, but specifically comprise Thiol proteases, metalloproteases, Trypsin, Chymotrypsin, Endoproteinase Asp-N, Endoproteinase Arg-C, Endoproteinase Glu-C, Endoproteinase Lys-C, Thermolysin, Elastase, Papain, Proteinase K, Subtilisin, Clostripain, Exopeptidase, Carboxypeptidase A, Carboxypeptidase P, Carboxypeptidase Y, Cathepsin C, Acylaminoacid-releasing enzyme, and Pyroglutamate aminopeptidase.

Fabric Materials, Functionalization and Incorporation of Enzymes

Fabrics used in the invention include melt-blown, meltspun, spun-lace or spun-bound polypropylene. Also used are natural fibers such as bamboo, jute, soy and hemp which are all sustainable and environmentally friendly. Cotton and silk may also be used. Blends of any of the above may also be used. In a typical embodiment using materials most used for making masks, the materials for structural components are as follows. The inner layer is made of non-woven spunbond polypropylene (20 gsm). It is fluid absorbent. The middle layer is made of meltblown polypropylene (25 gsm). The outer layer is made of spunbond polypropylene (20 gsm). A hydrophobic outer coating is added which will reject a certain percentage if droplets. Others will penetrate and react with enzyme-activated layer. Inner and outer layers optionally blended with cotton and other Non-woven fabrics.

Another type of new fabric that may be used is one made from the process described in US patent application 20010007005 "A process for flash spinning polymethylpentene alone or as a blend with polyethylene or polypropylene using various spin agents having essentially zero or very low ozone depletion potential" and in 20010006729, both to DuPont.

A typical surgical mask is manufactured from a nonwoven multi layered design comprising of a layer of polypropylene with an inner layer of melt blown and a further layer of polypropylene. They are ultra-sonically welded to provide additional strength. Material Content is as follows: Front layer 18-20 gsm spunbond polypropylene, inner layer 20-25 gsm melt blown filter, reverse layer 25 gsm spunbond polypropylene. Dimensions—standard mask is 95 mm width by 175 mm length.

Other synthetic textile structures that may prove useful in the present invention include spunlace polypropylene spunbond polypropylene. Spunbond polypropylene and non woven spunlace (also known as hydroentangled, jet entangled or spunlaced) are suitable for masks and many PPE materials. The main bonding processes used for nonwoven fabrics are either chemical, thermal, hydro entanglement or mechanical. In the bonding of spunbond polypropylene, "calendering" is used, where the fibres are calendered through heated rollers to bond them. Spunbond polypropylene can be pinsonically welded using ultrasonic energy to form quilted products particularly suited to masks. Spunlace is particularly suitable for masks and disposable bedding due to its soft feel, and can be manufactured in polypropylene or spun-melt-spun. See https://www.textileinnovations.co.uk/portfolio-view/disposable-healthcare-products.

Biodegradable mask: A bamboo mask coated with chitosan (optionally cross-linked together), with the enzymes adsorbed or covalently attached to the chitosan to make a fully biodegradable mask.

Electrospun materials: Enzymes can be immobilized on electrospun polymer nanofibers (Wang et al 2009 J. Molecular Catalysis B: Enzymatics 56:189-195. Electrospun nanofibers with reactive surfaces may support enzymes immobilization either as monolayers or aggregates.

As discussed elsewhere in this disclosure, the masks of the invention may have layers additional to the enzymatic layer. These layers may act to trap or inactivate pathogens by using either biochemical means (e.g., other enzymes, polyphenols etc.), chemical means (citrate, salts, phenols etc.) or by physical means (e.g., electrostatic, hydrophobic or hydrophilic surfaces, biostatic finish based on anchored trihydoxysilyl long chain quaternary ammonium salts etc.).

In certain embodiments the mask may include a hydrophobic inner layer to trap particle-containing aerosols. In some of these embodiments the hydrophobic inner layer may include enzymes so that pathogens attracted to the hydrophobic regions, trapped and inactivated.

Corona treatment is one preferred way to functionalize PP before addition of proteins/enzymes. Corona treatment creates —OH functional groups that the enzymes will bind to. Corona treatment (sometimes referred to as air plasma) is a surface modification technique that uses a low temperature corona discharge plasma to impart changes in the properties of a surface. The corona plasma is generated by the application of high voltage to an electrode that has a sharp tip. The plasma forms at the tip. A linear array of electrodes is often used to create a curtain of corona plasma. Materials such as plastics, cloth, or paper may be passed through the corona plasma curtain in order to change the surface energy of the material. All materials have an inherent surface energy. Surface treatment systems are available for virtually any surface format including dimensional objects, sheets and roll goods that are handled in a web format. Corona treatment is a widely used surface treatment method in the plastic film, extrusion, and converting industries. See Martina Lindner, J. APPL. POLYM. SCI. 2018, DOI: 10.1002/APP.45842 and Chiara Mandolfino Polymers (Basel) v.11 (2); 2019 FebPMC6418568, Functionalization of Neutral Polypropylene by Using Low Pressure Plasma Treatment: Effects on Surface Characteristics and Adhesion Properties.

Electret fabrics are electrostatically charged, and may also be used to increase filtration efficiency of disposable masks, such as the fabrics used in the middle layer of N95 masks. The high-voltage corona charging method is the most widely used electret treatment method in industrial production. The principle is to use the ion beam produced by the corona discharge phenomenon of the local breakdown of air caused by a non-uniform electric field to bombard the dielectric and charge it. The higher the charging voltage, the stronger the electric field strength formed. The literature suggests that filtration efficiency of 20 g/m2 melt-blown fabric increases from 26.5% before the electret treatment to 79.5% after the treatment, and the filtration efficiency of 40 g/m 2 meltblown nonwoven fabric Increased from 51.8% before electret treatment to 95.62% after treatment.

Non-woven fabric with electret treatment can be incorporated in to the PPE materials/masks of the invention, providing a layer with high filtration efficiency. Since electret materials may lose their effectiveness with washing, these layers may be incorporated into a mask or other PPE material subsequent to any washing or rinsing step. For example, in a typical method, electret fabrics may be ultra-sonically welded onto the enzyme-containing mask material. It may be incorporated into a middle layer, as is typical for an N95 mask or into any other interior or exterior later. Enzymes may be incorporated into the electret layer, but it is anticipated that the electret layer and the enzyme layer would generally be separate layers.

Biodegradability and sustainability is a very important factor for the next generation of PPE. Polypropylene is not biodegradable or sustainable. Natural biodegradable materials are preferably used to make PPE of the invention. Natural textiles include (but are not limited to) those made from bamboo, jute, soy, chitosan, seaweed and hemp, which are all sustainable and environmentally friendly. Natural sustainable textiles are preferred and are very important for the biodegradable embodiments of the present invention, which are foreseen as the main commercial versions. Bamboo and soy and chitosan textiles are the preferred embodiment partly because they are naturally antimicrobial. Cotton and silk may also be used, though are less sustainable and have a bigger carbon footprint. Materials made from bio-based renewable resources in the form of bamboo species have several advantages which include its fast renewability, its biodegradability, its efficient space consumption, its low water use, and its organic status. The advantages of bamboo fabric are its very soft feel (chemically-manufactured) or ramie-like feel (mechanically-manufactured), its antimicrobial properties, its moisture wicking capabilities and its anti-static nature. See: Sustainable Textiles: the Role of Bamboo and a Comparison of Bamboo Textile properties, January 2010Journal of Textile and Apparel, Technology and Management 6(3), Marilyn Waite, and Allwood, J et al. (2006) and The present and future sustainability of clothing and textiles in the United Kingdom., S. N., Biswal, et al. Biodegradable Soy-Based Plastics: Opportunities and Challenges. Journal of Polymers and the Environment 12, 35-42 (2004), all incorporated by reference herein.

Other textiles that may be used include those made from protein fibers from natural animal sources through condensation of a-amino acids to form repeating polyamide units with a various substituent on the a-carbon atom. In general, protein fibers are fibers of moderate strength, resiliency, and elasticity. They have excellent moisture absorbency and transport characteristics. They do not build up a static charge. Example of some these fibers is Wool, Silk, Mohair, Cashmere etc.

Bamboo and soy-based materials can be used to produce both the fabric portion and the rigid parts of the mask/PPE.

Chitosan is another highly attractive biodegradable and sustainable material that can be used to supply the fabric portion of the masks of the invention. It is also very well suited for attachment of enzymes. It can also be used to make the rigid components like the nose piece. Chitosan is the deacetylated derivative of chitin, the second most abundant polysaccharide on earth after cellulose. Chitosan itself has antimicrobial activity due to its polycationic nature. It is non-toxic, biocompatible and biodegradable. Adhesion of chitosan to cellulose is weak, but it has been cross-linked to cotton using dimethylol dihydroxy ethylene urea, polycarboxylic acids including citric acid, and derivatives of imidazolidinone. Cross-linking is by hydroxyl groups and lasts up to 50 washes. Enzymes will adsorb onto the chitosan. Covalent linkage can also be used in other embodiments. See Troynikov et al., Sustainable Automotive Technologies 2012 (pp. 81-89) Edition: 1stChapter: New Automotive Fabrics with Anti-odour and Antimicrobial Properties, New Automotive Fabrics with Anti-odour and Antimicrobial Properties. Also Zhang Z, Chen L, Ji J, Huang Y, Chen D. Antibacterial Properties of Cotton Fabrics Treated with Chitosan. Textile Research Journal. 2003; 73 (12):1103-1106.

Chitosan can easily be adapted to bind proteins, either by physical adsorption, or by functionalization allowing covalent bonding. In a first approach, amino groups of chitosan can be functionalized with tris(2-aminoethyl)amine to produce amine double-branched moieties, which are subsequently activated with glutaraldehyde. In a second approach, chitosan beads are directly modified by glutaraldehyde to produce aldehyde groups. Covalent immobilization of proteins/enzymes can then be performed. See Simin Khodaei, Samira Ghaedmohammadi, Mehdi Mohammadi, Garshasb Rigi, Parisa Ghahremanifard, Reza Zadmard, Gholamreza Ahmadian, Covalent Immobilization of Protein A on Chitosan and Aldehyde Double-Branched Chitosan as Biocompatible Carriers for Immunoglobulin G (IgG) Purification, Journal of Chromatographic Science, Volume 56, Issue 10, November 2018, Pages 933-940.

Structural elements of the PPE of the invention have generally been addressed in the art. In general the material will be pleated and ear loops and polypropylene-covered aluminum bendable nose piece will be added. In other embodiments both the ear loops and the nose piece will be made of a biodegradable material such as bamboo or soy, which can easily be produced in any number of shapes in much the same way as plastics are sculpted. Thus different nose shapes can be accommodated.

Enzymes are stably incorporated into the fabrics my various means such as by electrostatic, electrovalent, non-covalent or covalent means. Materials may be used in their native manufactured form or may be functionalized. Immobilization on fabric may be accomplished by Adsorption, covalent attachment to functionalized material, monolayer or aggregate. Each can be done with or without $Ca^{2+}$ ions present.

In a simple method, a cocktail of proteases and lipases at specific concentrations in aqueous solution (optionally including other components) is applied by spraying/soaking, and will adsorb onto the material during drying. This may be done at room temperature or elevated temperature to decrease drying time. Adsorption is mediated by non-covalent means, such as by ionic and electrostatic interactions. The materials are incubated for up to 24 hours at room temperature or at an elevated temperature. The dried materials may then optionally be rinsed to dissociate unbound material. The material is then dried and rolled for shipment/manufacture.

Enzyme may also be ionically immobilized onto the material by functionalizing the polypropylene or other materials. A simple method involves pre-treating polypropylene with allylamine gas to produce primary amine groups on the surface, then adding the enzymes to the treated material in the presence of excess $Ca^{2+}$. Adsorption will occur by ionic interactions and should be strong. Large negatively charged regions on enzyme surface adsorb to the positively charged amine groups on the polypropylene fibers. The same process can be done with other fibers including bamboo, soy, hemp and jute. The textile products are then dried and rolled for shipment and manufacture.

A very interesting broadly applicable adhesion promoter has been developed for polypropylene by using fusion proteins plus anchor peptides. It has long been appreciated that surface modification of polypropylene is required for its application as textile fibers or filtration membranes. Modification of polypropylene is challenging due to absent functional surface groups. An anchor-peptide-based toolbox for green and versatile polypropylene functionalization has been developed by Kristin Rübsam et al., Polymer Volume 116, 5 May 2017, Pages 124-132Anchor peptides: A green and versatile method for polypropylene functionalization. Fusion proteins composed of enhanced green fluorescent protein (EGFP) and anchor peptides (e.g. cecropin A or LCI) were designed and applied to polypropylene surfaces. The fusion protein EGFP-LCI forms densely packed monolayers of 4.1±0.2 nm thickness. Washing of EGFP-LCI coated polypropylene with 10 mM non-ionic surfactant (Triton X-100) did not detach the protein film, whereas EGFP was removed completely. Anchor peptides promote binding to polypropylene by simple dip-coating at room temperature in water. The high coating density (0.8 pmol/cm2) as well as the number and diversity of provided functional groups offer a viable alternative to conventional modification strategies of functionalizing polypropylene. LCI's role as broadly applicable adhesion promoter was demonstrated by equipping polypropylene with the fluorescent dye ThioGlo-1 via the anchor peptide LCI.

Another embodiment for functionalizing the fabric is by alumoxane treatment of polypropylene. This makes the material surface hydrophilic. The surface of this alumoxane-treated PP is then functionalized with cysteic acid to generate a filter with the useful characteristic that it allows water to pass through, but resists the passage of other things such as organic and inorganic chemicals. The surface is covered with closely spaced positively charged amine groups and negatively charged sulfonic acid group. The coating is highly hydrophilic and is being used to clean up fracking waste water. Alumoxane treatment may be used with polypropylene or any other appropriate material.

Another embodiment can include PPE materials made using super-hydrophobic polypropylene fibers (optionally hollow fibers). The polypropylene fiber is combined with silica particles to preparation the super-hydrophobic coatings. The fibers are then modified by 1H,1H,2H,2H-Perfluorooctyltriethoxysilane (POTS) that exhibited a super-hydrophobic surface with a static water contact angle of 157 degrees. See Fabrication of super-hydrophobic polypropylene hollow fiber membrane and its application in membrane distillation Author links open overlay panel, ZhihaoXu Desalination Volume 414, 15 Jul. 2017, Pages 10-17.

In various embodiments it is advantageous to modify polypropylene fibres so that they better retain enzymes, either electrostatically or by other non-covalent means or covalently. Many methods may be used including modification of polypropylene fibres with cationic polypropylene dispersion. The absence of functional groups on the surface of polypropylene (PP) fibres and low polarity make PP fibres a challenging substrate for adherence of other moieties. This is a well-known problem in dying, and techniques have been developed for the mass coloration of fibres. Mass coloration during fiber extrusion is the major technique applied today. A new method to modify the surface of PP fibres utilizes the deposition and thermal fixation of cationic PP dispersion. Through padding and thermal fixation of a cationic PP dispersion, dyeable 100% PP fibres can be obtained. The potential of this new method to produce surface-modified 100% PP fibres may be useful to the present invention. See Modification of polypropylene fibres with cationic polypropylene dispersion for improved dyeability, July 2018 Tom Wright, Coloration Technology 134(5).

Conventionally, functionalization of PP with MA is achieved via melt processing. Polypropylene can also be functionalized by a process preferably by maleation of polypropylene by use of a selected class of peroxides which will not cause the molecular weight of the polyolefin to significantly degrade, described in WO1990013582, PCT/US1990/002189, to Exxon Chemical Patents Inc. Also see Functionalization of polymers, including polyolefins, with a, (3-unsaturated carboxy-derived moieties through the use of solid-state shear pulverization, WO2014047591, U.S. 61/704,096 to Northwestern University.

Another functionalization method is described in Preparation and Characterization of Functionalized Polypropylene with Acrylamide and Itaconic Acid by Oromiehie et al., Journal of Materials Science and Chemical Engineering, 2014, 2, 43-51.

Also see Ozen, I., Rustal, C., Dirnberger, K. et al. Modification of surface properties of polypropylene films by blending with poly(ethylene-b-ethylene oxide) and its application. Polym. Bull. 68, 575-595 (2012), which describes improving the interfacial adhesion between polypropylene (PP) and polyamide layers (PA) has been investigated by means of addition of commercially available amphiphilic poly(ethylene-b-ethylene oxide) (P(E-b-EO)) block copolymers.

Atmospheric Pressure Plasma can also be used to enhance protein binding. PP fabrics can be chemically and physically modified by Low Temperature Atmospheric Pressure Plasma (APP). It can be used to treat large area samples directly on-line, thanks to the combination with a roll-to-roll system and has a low-environmental impact for surface functionalization involving O- and N-functionalizing gas mixtures. See Rombolà et al., Czechoslovak Journal of Physics, Volume 56, Issue 2, pp. B1021-B1028. Other methods for functionalizing/coating polypropylene are found for example in the following US patent references: U.S. Pat. Nos. 2,998,324A 82,872,359A 2,998,324A 2,998,324 A 2,998,324 A 2,998,324A 82,872,359 A 82,872,359 A 82,872, 359A 2,998,324 A 2,998,324 A 2,998,324.

Of course, the improved and desired applications of the present invention are to create fully biodegradable masks and PPE. This involves using fully biodegradable fabrics made from chitosan, soy, hemp, jute or bamboo. These are easy to functionalize. The adsorption of proteins onto cellulose fibers is well known. Cellulose binding domains (CBDs) are active in the adsorption. See Liu, J., and Hu, H. (2012): The role of cellulose binding domains in the adsorption of cellulases onto fibers and its effect on the enzymatic beating of bleached kraft pulp, BioRes. 7(1), 878-892. And see Biotechnology Advances: Levy, Volume 20, Issues 3-4, November 2002, Pages 191-213, Cellulose-binding domains: Biotechnological applications. And see Biomacromolecules 2019, 20, 2, 769-777, Jan. 18, 2019. Covalent binding of proteins such as enzymes to cellulose may be achieved in many ways known in the art including those described in J Appl Biochem. October-December 1984; 6 (5-6):367-73. New method for covalent immobilization of proteins to cellulose and cellulose derivatives, M A Krysteva, S R Blagov, T T Sokolov, and Covalent binding of proteins and glucose-6-phosphate dehydrogenase to cellulosic carriers activated with s-triazine trichloride Analytical Biochemistry, Volume 61, Issue 2, October 1974, Pages 392-415, and Enzyme immobilization to ultra-fine cellulose fibers via Amphiphilic polyethylene glycol spacers, September 2004, Journal of Polymer Science Part A Polymer Chemistry 42(17):4289-4299, and Immobilization-Stabilization of Proteins on Nanofibrillated Cellulose Derivatives and Their Bioactive Film Formation, February 2012 Biomacromolecules 13(3):594-603

Further Related Embodiments

The present invention lends itself to many different embodiments and variations, all of which fundamentally involve the use of psychrophilic proteases stably associated with a fabric which enzymes inactivate viral and other pathogens. However, during development of the invention, the inventors conceptualized various other embodiments and inventions, some of which are set out below.

In one alternative embodiment the enzymes may be supplied in the form of a liquid or a spray allowing consumers to revitalize their own masks after laundering.

In certain embodiments the invention provides not a material, but a spray comprising various proteases, specifically the GRAS proteases, specifically GRAS proteases derived from psychrophiles such as cod or crabs. Such proteases are very stable and safe and may be sprayed directly onto any fabric such as a face mask worn by the public. These enzymes might also be sprayed onto N95 respirators in situations that require extended use or re-use of the respirator. Similarly, a revitalizing enzyme spray could be used on surgical masks in healthcare and hospital environments, where the normally disposable masks are being reused due to manufacture or supply issues In another embodiment the invention may include antiviral compounds derived from algae, particularly polysaccharides such as sulphated polysaccharides from cyanobacteria such as Arthrospira Spec. or any compound disclosed in one of the following: US 20200276251 USE OF CYANOBACTERIAL BIOMASS IN TREATING HEPATITIS B VIRUS INFECTION; US 20200197458 CYANOBACTERIAL EXTRACTS, PROCESSES FOR PREPARING THE SAME AND USES THEREOF; US 20140127336 Process for the Preparation of a Pharmaceutically Effective Extract from Arthrospira Spec.; and US 20030078233 An antiviral composition containing as the active ingredient an antivirally-effective amount of a red microalga polysaccharide, or a mixture of two or more red microalga polysaccharides. Fucoidan from seaweed (*Fucus vesiculosus*) is a sulfated polysaccharide with antiviral activity, and is GRAS (Generally recognized as safe) since 2016. See Phytomedicine 1999 November; 6(5):335-40 and https://pubmed.ncbi.nlm.nih.gov/23234372/.

In another alternative embodiment a reporter assay may be incorporated into the PPE of the invention. In this case a peptide cleavage-induced reporter produces a signal that reports enzymic activity with a color change. This could also be applied on a discrete spot on the mask to monitor mask integrity if repeatedly used.

In another alternative embodiment the mask is fitted with a pressure sensor inside the mask such that mask fitting can be tested. This involves forcefully inhaling or exhaling when the mask is worn. If the mask is properly-fitted, inhaling will cause a rapid but temporary pressure drop inside the mask, and exhaling will cause a rapid but temporary pressure drop rise inside the mask. But if not properly fitted, forcefully inhaling or exhaling will not cause such a large pressure change, if any, because air will travel without resistance through the gaps in the poorly-fitted mask. The key component for such a pressure sensor application for correct fitting can be purchased commercially, for example the Honeywell "MicroPressure MPR Series" which is pre calibrated and compensated with high accuracy as low as ±1.5% FSS TEB and provides a digital output. (https://sps.honeywell.com/us/en/products/sensing-and-iot/sensors/pres sure-sensors/board-mount-pressure-sensors/micropres-sure-mpr-series). This can be in functional contact with a circuit comprising an alert means, such as a sound alert or light alert, and may also include an on/off switch and a battery. Because the sensor would only function above or below a certain set pressure range, the alert means would not be activated except when the target pressure is reached. The user could test the mask fitting by placing the mask on the face, adjusting it for fit, then inhaling or exhaling forcefully. If correctly fitted, the alert means would activate, and a sound and/or light would be activated, letting the user know that the mask is properly fitted. An appropriate pressure drop or increase to which the pressure sensor may be set might be, for example, 1-2 psi. This exemplary pressure is not to limit the invention.

Measuring Virus Inactivation

Viral inactivation was performed according to ASTM International E1052-11 method "Standard Test to Assess the Activity of Microbicides against Viruses in Suspension". See, Stefansson et al 2017, A medical device forming a protective barrier that deactivates four major common cold viruses, Virology: Research and Reviews doi: 10.15761/VRR.1000130. Enzyme and virus were mixed together at 35-37° C. (slightly above the temperature of exhaled breath at 34° C.) for 20 minutes. The enzyme was neutralized before the mix was added to host cells. Cells were incubated for 90-100 minutes before being washed and plated. Cultures were scored for viral-induced cytopathic effects. Viral titer was calculated as log 10 TCID50/ml (50% tissue culture infection dose).

Efficiency of the invention is measured in terms of inactivation of the virus over time in a controlled experiment. A standard measureable value of inactivation is $>T_{90}$ which is defined as the time for at least 90% inactivation of the viral population (measured as PFUs) a controlled assay. In the present disclosure, the invention in the form of a paper fabric surgical mask impregnated with proteases and lipases, and sprayed with a viral load from an atomizing spray bottle, has a $>T_{90}$ of about 3 to 20 minutes.

Using the Enzymatica data, reduction of over 90% of virus was achieved in a 20 minute assay. All viruses except for adenovirus will likely take less than 20 minutes to deactivate 90% because all have over 1.0 log 10 reductions in the 20 minutes.

$T_{90}$ can be between 30 seconds and 30 minutes depending on various factors such as the moisture of the mask and the viral load distributed onto the mask surface, preferably from 1 minute to 15 minutes under experimental conditions. It is believed that, under constant atmospheric humidity, the longer the mask is worn, the greater the moisture in the mask will be, and therefore the faster the solubilization of the enzymes. However, viral particles will inherently be carried in water droplets, which should provide a suitable environment for enzyme solubilization as soon as the droplet contacts the fabric.

A typical virus used in a control assay is uses an enveloped virus pseudotype. Coronaviruses and other pseudo-typed viruses may be used. In a standard assay, $T_{15/30/90}$ etc. can be measured. Experientially, a solution of $\phi 6$ is sprayed onto a test mask from a distance of 10 cm at a total spray volume of 0.5 ml, and at a $\phi 6$ viral concentration of $10^4$ to $10^5$ plaque forming units per ml (PFUs/ml), with humidity maintained at 55% and temperature maintained at 23 degrees Centigrade. Samples are taken at various times and plaque formation is measured over time. See Whitworth et al AEM Accepted Manuscript Posted Online 26 Jun. 2020 Appl. Environ. Microbiol. doi:10.1128/AEM.01482-20; and Nathalia Aquino de Carvalho et al., Evaluation of Phi6 Persistence and Suitability as an Enveloped Virus Surrogate Environ. Sci. Technol. 2017, 51, 15, 8692-8700; and Baize et al., Emergence of Zaire Ebola Virus Disease in Guinea N. Engl. J. Med. 2014, 371 (15) 1418-1425; all of which are incorporated by reference herein for all purposes.

In alternate embodiments, the invention may provide an inactivation efficiency of >$T_{70}$ (time to >70% inactivation measured by reduction in PFUs) of about 3 minutes. $T_{70}$ can be between 30 seconds and 60 minutes depending on various factors such as the moisture of the mask and the viral load distributed onto the mask surface. Preferably $T_{70}$ (or above) will be achieved between 1 min and 20 mins under standard conditions. Standard conditions are, for example, spraying a solution of ϕ6 onto a test mask from a distance of 10 cm at a total spray volume of 0.5 ml, and at a ϕ6 viral concentration of $10^4$ to $10^5$ plaque forming units per ml (PFUs/ml), with humidity maintained at 55% and temperature maintained at 23 degrees Centigrade.

In another alternate embodiments, the invention may provide an inactivation efficiency of >$T_{90}$ of about 1-20 mins, preferably 3-7 mins. In another alternate embodiments, the invention may provide an inactivation efficiency of >$T_{90}$ of 10-60 mins. In another alternate embodiments, the invention may provide an inactivation efficiency of >$T_{70}$ of 3-7 mins. In another alternate embodiments, the invention may provide an inactivation efficiency of >$T_{50}$ of 3-7 mins. The fabric/mask of the invention does not have to achieve any specific inactivation efficiency with any particular virus, and any of these disclosed efficiencies will be sufficient to provide an effective reduction in viral infectivity. For example a 50% reduction over a period of an hour will significantly reduce the potential infective potential of a mask if left overnight.

It should be noted that since the enzymes are activated by an aqueous environment, lightly misting the mask after use (or during use) may enhance enzyme activation and increase efficiency of pathogen inactivation, and this may be done periodically while in use.

Methods of Preparation

Common fabrics can be used for the structural part of the invention. In a typical example, the inner layer is made of a non-woven spunbond polypropylene (20 gsm) which is fluid absorbent. The middle layer is made of meltblown polypropylene (25 gsm). The outer layer is made of spunbond polypropylene (20 gsm). A hydrophobic outer coating is provided that will reject a certain percentage if droplets, but others will penetrate and react with enzyme-activated layer. Inner and outer layers optionally blended with cotton and other Non-woven fabrics. The materials can be pleated, ear loops and polypropylene-covered aluminum bendable nose piece will be added. A trademark and trade-dress color/design can be added. Note that preferred 2nd generation products use fabrics made from chitosan, soy, hemp, jute, bamboo or cotton and are fully biodegradable.

Preferred embodiments use biodegradable fabrics. Enzymes may be incorporated into the fabrics by various means such as spraying or by adding enzymes to the pulping or washing phases of manufacture, prior to the dewatering phase. Since the proteases are highly stable, they can be dried, and enzyme-impregnated fabrics can be dewatered, and yet the enzymes will maintain their ability to perform their catalytic functions when exposed to a micro-aqueous environment. It is important to avoid high temperatures during the manufacturing process. The enzymes should not be exposed to temperatures above 45° C.

The concentration of enzymes in the pulp/wash solution can be determined empirically. A typical concentration in the wash solution for Serine proteases is 20 mg/ml. In other embodiments the concentration may be from 1000 mg/ml to 5 mg/ml. In another embodiment, a protease and/or lipase solution can be sprayed onto a fabric of any kind, and subsequently dried. A typical concentration in the spray solution for proteases and/or lipases is 20 mg/ml. This should provide sufficient coverage to create a fabric with desirable viral inactivation efficiency, with a $T_{90}$ can be between 30 seconds and 60 minutes. Other concentration may be from 5 mg/ml to 1000 mg/ml.

Finally, important embodiments include PPE that is biodegradable or recyclable, and made from sustainable sources. With billions of polypropylene masks being produced and disposed of every year, biodegradability and sustainability is a very important factor for the next generation of PPE. Natural textiles include (but are not limited to) those made from bamboo, jute, soy, chitosan, seaweed and hemp. Bamboo and soy and chitosan textiles are the preferred embodiment partly because they are naturally antimicrobial.

Experimental Data 1—Protease Activity of ColdZyme Vs Bovine Trypsin

Concentration of the trypsin in ColdZyme was calculated using a BCA protein assay and was 100 micrograms/ml. We note that Bovine trypsin is 1 mg/ml.

ColdZyme activity study.

ColdZyme protease activity was compared to trypsin:

1. At 40° C. for 30 mins
2. At room temperature (about 20° C.) for 3.5 hours
3. At 4° C. for 24 hours Activity is shown as A492 nm (a proxy for protease activity based on digestion of FTC-casein)

| | 40° C. | 20° C. | 4° C. |
|---|---|---|---|
| Trypsin | 0.573 | 0.514 | 0.525 |
| ColdZyme (neat - 1) | 0.382 | 0.355 | 0.326 |
| ColdZyme (neat - 2) | 0.376 | 0.367 | 0.331 |
| ColdZyme (1/10 - 1) | 0.176 | 0.195 | 0.211 |
| ColdZyme (1/10 - 2) | 0.172 | 0.196 | 0.215 |

The positive control bovine trypsin is supplied at 1 mg/ml in the presence of 10 mg/ml BSA.

Experimental Data 2—Activity of ColdZyme Trypsin on Bamboo Fabric

ColdZyme trypsin on bamboo fabric at 37° C.–activity=30 au/hr/mg

ColdZyme trypsin on bamboo fabric at 16° C.–activity=16.5 au/hr/mg

Bovine trypsin on bamboo at 37° C.–activity=0.68 au/hr/mg

Bovine trypsin on bamboo at 16° C.–activity=0.65 au/hr/mg

Note that the cod enzyme is much more active than bovine trypsin at either temperature. The cod enzyme is only about half as active at 16° C. compared to 37° C.; the optimum temperature of this enzyme is over 37° C. The bovine trypsin had almost exactly the same activity at both temperatures.

Experimental Data 3—Protease Activity of Fabric Associated ColdZyme Vs Bovine Trypsin at 37° C. and 16° C.

ColdZyme trypsin and control bovine trypsin were added to bamboo fabric by adsorption. 200 microliters (200 micrograms) of bovine trypsin was adsorbed to each 1 cm2 piece of fabric. 200 microliters of a 1/5 dilution of ColdZyme trypsin (4 micrograms) was adsorbed to similar 1 cm2 pieces of bamboo fabric. Fabrics were dried overnight prior to being tested in the protease assay.

Assays were performed at 37° C. for 1 hour and 2 hours using digestion of FTC-casein and Absorbance at 492 nm as a proxy for protease activity. For each assay one quarter of a 1 cm2 piece of fabric was included in the incubation buffer.

| | | |
|---|---|---|
| ColdZyme fabric square 1 | 1 hr Ab492 nm - 0.207 | 2 hrs Ab492 nm - 0.239 |
| ColdZyme fabric square 2 | 1 hr Ab492 nm - 0.225 | 2 hrs Ab492 nm - 0.253 |
| Bovine trypsin fabric | 1 hr Ab492 nm - 0.580 | 2 hrs Ab492 nm - 0.614 |

Change in Ab492 nm per hour is (averaged) 0.03 for ColdZyme and 0.034 for bovine trypsin at 37° C.

Change in Ab492 nm (absorbance units or au) per hour per ml of enzyme solution was:

ColdZyme on fabric at 16° C.=0.6 au/hr/ml
Bovine trypsin on fabric at 16° C.=0.68 au/hr/ml
Experiment was repeated at 16° C.

For this experiment, the 1 cm2 piece of bamboo with bovine trypsin adsorbed was cut into ⅛th squares.

¼ squares of the ColdZyme fabric was used as previously.

Enzyme activity was measured after 4 and 8 hours.

| | | |
|---|---|---|
| ColdZyme fabric square | 4 hrs Ab492 nm - 0.143 | 8 hrs Ab492 nm - 0.209 |
| Bovine trypsin fabric | 4 rhs Ab492 nm - 0.507 | 8 hrs Ab492 nm - 0.564 |

Change in Ab492 nm (absorbance units or au) per hour per ml of enzyme solution was:

ColdZyme on fabric at 16° C.=0.33 au/hr/ml
Bovine trypsin on fabric at 16° C.=0.648 au/hr/ml Note: these activities are per ml of enzyme solution. The Bovine trypsin was provided at 1 mg/ml in PBS with 10 mg/ml BSA as a stabilizing agent. The concentration of the ColdZyme enzyme is 100 micrograms/ml. For these assays, at least 10-fold less ColdZyme enzyme was added to the fabric than bovine trypsin.

Purification of trypsin: The present invention preferably uses psychrophilic proteases from crustations or cod. Purification of trypsin mixes from fish/crustation waste may be performed as follows: (i) Prepare crude material—isolate intestines (incl. pyloric cecum or hepatopancreas). (ii) Homogenize tissue. (iii) Extract crude enzymes—centrifugation, precipitation, and/or fractionation. (iv) Purify enzymes—gel filtration, ion exchange, hydrophobic interaction and/or affinity chromatography. Purification of enzymes from cold water crab species hepatopancreas would be performed similarly.

Terms and Definitions

In the present disclosure, we may discuss enzyme activity. This can be confusing since there are several units of enzyme activity commonly in use. In this disclosure enzyme activity is expressed as change in absorbance units at 492 nm over time based on digestion of FTC-casein in a modification of Twining (1984), as used in the Calbiochem Protease Assay Kit (Cat No. 539125). Commonly, however, enzymatic activity is normally described as mol/min (the number of μmol of substrate converted per minute). See Eur. J. Biochem. Y7, 319-320 (1979) Nomenclature Committee of the International Union of Biochemistry (NC-IUB) Units of Enzyme Activity Recommendations 1978. On the other hand, a more useful and practical measure of the efficiency of the fabrics of the invention is the inactivation efficiency, expressed as, for example, $T_{90}$, the time required to inactivate 90% of the pathogens, for example reducing PFUs by 90%. $T_{90}$ can be measured using the non-pathogenic enveloped bacteriophage Phi6 ($\phi6$) as a surrogate for enveloped waterborne viruses. Experimentally, a solution of $\phi6$ is sprayed onto a test mask from a distance of 10 cm at a total spray volume of 0.5 ml, and at a $\phi6$ viral concentration of $10^4$ to $10^5$ plaque forming units per ml (PFUs/ml), with humidity maintained at 55% and temperature maintained at 23° C.

Room temperature as used herein spans the usual temperatures for a room, and may be from 8° C. to 35° C. or 10° C. to 30° C., or 12° C. to 27° C., more preferably from 13° C. to 25° C., more preferably from 15° C. to 24° C.

Proteases catalyze the breakdown of proteins into smaller polypeptides or amino acids by cleaving peptide bonds by hydrolysis.

Lipases catalyze the hydrolysis of lipids and are a subclass of the esterases.

Amylases catalyze the hydrolysis of starch into sugars.

Cellulases catalyze the decomposition of cellulose into simpler sugars. 'Fabrics' in this disclosure include any materials that can be formed into flexible sheets capable of being made into clothes sheets and the like.

'Impregnated', in the present disclosure, refers to a substance that is incorporated into and throughout a substrate; when this word is used, the term 'sprayed' is inherently implied unless specifically excluded.

'Sprayed', in the present disclosure, refers to a substance that is deposited onto a surface, and where used can equally be substituted with the action of painting, dipping or any other method to apply a substance onto a surface.

'Virus/virion', in the present disclosure, refers to an obligate parasite without independent metabolism outside the host cell.

'Inactivate', in the present disclosure, refers to the substantial reduction or elimination of the ability of an organism (including a virus) to reproduce.

'Mask', in the present disclosure, refers to any face-covering designed to restrict or prevent the flow of particulate matter from the environment into the respiratory system of an animal. The disclosure is not limited to masks and applies to worn fabrics, filters etc.

A 'paper-based fabric', in the present disclosure, refers to any fabric made from at least 50% paper or lignin material, preferably 60%, 75%, 80%, 90% or at least 95% paper or lignin material.

The word 'manufactured', in the present disclosure, means made, constructed, or in any way confected.

Biodegradable, in the present disclosure, refers to an ability to degrade over a period of time commensurate with the degradation of domestic waste products, such as months or years.

'Psychrophiles' or 'cryophiles' are defined as extremophilic organisms that are capable of growth and reproduction in low temperatures, ranging from −20° C. to +10° C. They are found in places that are permanently cold, such as the polar regions and the deep sea. They can be contrasted with thermophiles, which are organisms that thrive at unusually high temperatures, and mesophiles at intermediate temperatures.

'Psychrophiles' or 'cryophiles' are defined as extremophilic organisms that are capable of growth and reproduction in low temperatures, ranging from −20° C. to +10° C. They are found in places that are permanently cold, such as the polar regions and the deep sea. They can be contrasted with thermophiles, which are organisms that thrive at unusually high temperatures, and mesophiles at intermediate temperatures.

In this disclosure, a 'psychrophilic protease' is defined as a protease that is active at temperatures below 15° C. For example, we may say that a cold-active marine trypsin (i.e.

a trypsin derived from a species of fish or crustacean living in cold waters) has an activity of at least 0.04 au/hr/$cm^2$ at a temperature of 16° C. when adsorbed on fabric

REFERENCES

The following references and any and all references and publications mentioned in this disclosure are hereby incorporated by reference in their entirety for all purposes.

Niyonzima et al., Coproduction of detergent compatible bacterial enzymes and stain removal evaluation. J. Basic Microbiol. 2015 October; 55(10):1149-58.

Niyonzima et al., Detergent-compatible bacterial cellulases. FN. J Basic Microbiol. 2019 February; 59(2):134-147.

Niyonzima et al., Detergent-compatible bacterial amylases. Appl Biochem Biotechnol. 2014 October; 174(4):1215-1232.

Haddar A, et al., Two detergent stable alkaline serine-proteases from *Bacillus mojavensis* A21: purification, characterization and potential application as a laundry detergent additive. Bioresour Technol. 2009 July; 100 (13):3366-73.

Chen B. Y, et al., Utility of enzymes from *Fibrobacter succinogenes* and *Prevotella ruminicola* as detergent additives. J. Ind Microbiol Biotechnol. 2008 August; 35(8):923-30.

D'Souza N. M, et al., Membrane cleaning in the dairy industry: A review. Crit. Rev. Food Sci. Nutr. 45: 125-13, 2005.

M. Kavitha et al., Cold active lipases, an update, Frontiers in Life Science, 2016 V. 9, NO. 3, 226-238. Whitworth et al., AEM Accepted Manuscript Posted Online 26 Jun. 2020 Appl. Environ. Microbiol.

Nathalia Aquino de Carvalho et al., Evaluation of Phi6 Persistence and Suitability as an Enveloped Virus Surrogate Environ. Sci. Technol. 2017, 51, 15, 8692-8700.

Baize et al., Emergence of Zaire Ebola Virus Disease in Guinea N. Engl. J. Med., 371 (15) 1418-1425, 2014.

Stefansson, B., A. Gudmundsdottir, and M. Clarsund. 2017. A medical device forming a protective barrier that deactivates four major common cold viruses. Virology: Research and Reviews. 1:1-3.

Troynikov et al., Sustainable Automotive Technologies 2012 (pp. 81-89) Edition: New Automotive Fabrics with Anti-odour and Antimicrobial Properties Twining, S. S. 1984. Anal. Biochem. 143: 30.

Eur. J. Biochem. Y7, 319-320 (1979) Nomenclature Committee of the International Union of Biochemistry (NC-IUB) Units of Enzyme Activity Recommendations 1978

Troynikov et al., Sustainable Automotive Technologies 2012 (pp. 81-89) Edition: New Automotive Fabrics with Anti-odour and Antimicrobial Properties Zhang Z, et al. Antibacterial Properties of Cotton Fabrics Treated with Chitosan. Textile Research Journal. 2003; 73 (12):1103-1106.

Zhang et al., Journal of Integrative Medicine; Volume 18, Issue 2, March 2020, Pages 152-158, In silico screening of Chinese herbal medicines with the potential to directly inhibit 2019 novel coronavirus Kumar et al., 2008. Microbial Proteases and Application as Laundry Detergent Additive. Research Journal of Microbiology, 3: 661-672

Weinstein et al. Clinical Infectious Diseases, Volume 41, Issue 6, 15 Sep. 2005, Pages 848-854 Overview of Nosocomial Infections Caused by Gram-Negative Bacilli Kollef et al. Nosocomial Infection, Critical Care Medicine: February 2021—Volume 49—Issue 2—p 169-187.

Milanov et al. Gram-negative nosocomial infections in a general ICU: emerging new clues. Crit Care 15, P224 (2011).

International Patent No WO2013177834 A1 Marine bacteria cold-adapted protease and encoded gene and application thereof U.S. Pat. No. 8,759,065 B2 Protein and DNA sequence encoding a cold adapted subtilisin-like activity U.S. Pat. No. 9,574,185B2 Cold-adapted protease derived from *Pseudoalteromonas arctica* PAMC 21717 and uses thereof.

Feller, G., Gerday, C. Psychrophilic and/or cold active enzymes: hot topics in cold adaptation. *Nat Rev Microbiol* 1, 200-208 (2003). https://doi.org/10.1038/nrmicro773

The invention claimed is:

1. A material adapted to inactivate enveloped viruses present in an aqueous aerosol upon contact with the material, the material comprising a polypropylene fabric and a non-specific protease associated with the fabric, wherein said protease is a cold-adapted trypsin with an activity of at least 0.04 au/hr/cm2 at a temperature of 16 degrees Centigrade, wherein said cold-adapted trypsin is derived from a fish or a crustacean, and wherein the protease is bound to the fabric by adsorption.

2. The material of claim 1 wherein said protease is a Trypsin from one or more of Atlantic cod trypsin I, Atlantic cod trypsin X, Atlantic cod trypsin Y, Atlantic cod trypsin ZT, and Red king crab trypsin.

3. The material of claim 1 further comprising a salt selected from the group consisting of: sodium chloride, calcium chloride, potassium chloride, and sodium citrate.

* * * * *